US007557120B2

(12) United States Patent
Goble et al.

(10) Patent No.: US 7,557,120 B2
(45) Date of Patent: Jul. 7, 2009

(54) AMINOCYCLOPENTYL FUSED HETEROTRICYLICAMIDE MODULATORS OF CHEMOKINE RECEPTOR ACTIVITY

(75) Inventors: Stephen D. Goble, Edison, NJ (US); Alexander Pasternak, Princeton, NJ (US); Cheng Tang, East Brunswick, NJ (US); Changyou Zhou, Plainsboro, NJ (US); Lihu Yang, Edison, NJ (US)

(73) Assignee: Merck & Co., Inc., Rahway, NJ (US)

( * ) Notice: Subject to any disclaimer, the term of this patent is extended or adjusted under 35 U.S.C. 154(b) by 596 days.

(21) Appl. No.: 10/543,794

(22) PCT Filed: Feb. 23, 2004

(86) PCT No.: PCT/US2004/005297

§ 371 (c)(1), (2), (4) Date: Aug. 11, 2005

(87) PCT Pub. No.: WO2004/076411

PCT Pub. Date: Sep. 10, 2004

(65) Prior Publication Data

US 2007/0004714 A1 Jan. 4, 2007

Related U.S. Application Data

(60) Provisional application No. 60/449,547, filed on Feb. 24, 2003.

(51) Int. Cl.
*A61K 31/437* (2006.01)
*C07D 471/02* (2006.01)
*C07D 471/14* (2006.01)

(52) U.S. Cl. ........................................ 514/296; 546/81

(58) Field of Classification Search .................. 546/81; 514/296

See application file for complete search history.

(56) References Cited

OTHER PUBLICATIONS

Dorwald F. A. Side Reactions in Organic Synthesis, 2005, Wiley: VCH, Weinheim p. IX of Preface.*

* cited by examiner

*Primary Examiner*—Rita J Desai
(74) *Attorney, Agent, or Firm*—James L. McGinnis; Mark R. Daniel

(57) ABSTRACT

The present invention is directed to compounds of formulae (I and II)(wherein A, D, E, X, l, m, n and $R^1$ through $R^{18}$ are defined herein) which are useful as modulators of chemokine receptor activity. In particular, these compounds are useful as modulators of the chemokine receptor CCR-2.

15 Claims, No Drawings

AMINOCYCLOPENTYL FUSED HETEROTRICYLICAMIDE MODULATORS OF CHEMOKINE RECEPTOR ACTIVITY

CROSS REFERENCE TO RELATED APPLICATIONS

This application is the National Stage of International Application No. PCT/US2004/005297, filed 23 Feb. 2004 which claims the benefit under 35 U.S.C. 119(e) of U.S. Provisional Application No. 60/449,547, filed 24 Feb. 2003.

BACKGROUND OF THE INVENTION

The chemokines are a family of small (70-120 amino acids), proinflammatory cytokines, with potent chemotactic activities. Chemokines are chemotactic cytokines that are released by a wide variety of cells to attract various cells, such as monocytes, macrophages, T cells, eosinophils, basophils and neutrophils to sites of inflammation (reviewed in Schall, *Cytokine,* 3, 165-183 (1991) and Murphy, *Rev. Immun.,* 12, 593-633 (1994)). These molecules were originally defined by four conserved cysteines and divided into two subfamilies based on the arrangement of the first cysteine pair. In the CXC-chemokine family, which includes IL-8, GROα, NAP-2 and IP-10, these two cysteines are separated by a single amino acid, while in the CC-chemokine family, which includes RANTES, MCP-1, MCP-2, MCP-3, MIP-1α, MIP-1β and eotaxin, these two residues are adjacent.

The α-chemokines, such as interleukin-8 (IL-8), neutrophil-activating protein-2 (NAP-2) and melanoma growth stimulatory activity protein (MGSA) are chemotactic primarily for neutrophils, whereas β-chemokines, such as RANTES, MIP-1α, MIP-1β, monocyte chemotactic protein-1 (MCP-1), MCP-2, MCP-3 and eotaxin are chemotactic for macrophages, monocytes, T-cells, eosinophils and basophils (Deng, et al., *Nature,* 381, 661-666 (1996)).

The chemokines are secreted by a wide variety of cell types and bind to specific G-protein coupled receptors (GPCRs) (reviewed in Horuk, *Trends Pharm. Sci.,* 15, 159-165 (1994)) present on leukocytes and other cells. These chemokine receptors form a sub-family of GPCRs, which, at present, consists of fifteen characterized members and a number of orphans. Unlike receptors for promiscuous chemoattractants such as C5a, fMLP, PAF, and LTB4, chemokine receptors are more selectively expressed on subsets of leukocytes. Thus, generation of specific chemokines provides a mechanism for recruitment of particular leukocyte subsets.

On binding their cognate ligands, chemokine receptors transduce an intracellular signal though the associated trimeric G protein, resulting in a rapid increase in intracellular calcium concentration. There are at least seven human chemokine receptors that bind or respond to β-chemokines with the following characteristic pattern: CCR-1 (or "CKR-1" or "CC-CKR-1") [MIP-1α, MIP-1β, MCP-3, RANTES] (Ben-Barruch, et al., *J. Biol. Chem.,* 270, 22123-22128 (1995); Beote, et al, *Cell,* 72, 415-425 (1993)); CCR-2A and CCR-2B (or "CKR-2A"/"CKR-2A" or "CC-CKR-2A"/"CC-CKR-2A") [MCP-1, MCP-2, MCP-3, MCP-4]; CCR-3 (or "CKR-3" or "CC-CKR-3") [Eotaxin, Eotaxin 2, RANTES, MCP-2, MCP-3] (Rollins, et al., *Blood,* 90, 908-928 (1997)); CCR-4 (or "CKR-4" or "CC-CKR-4") [MIP-1α, RANTES, MCP-1] (Rollins, et al., *Blood,* 90, 908-928 (1997)); CCR-5 (or "CKR-5" or "CC-CKR-5") [MIP-1α, RANTES, MIP-1β] (Sanson, et al., *Biochemistry,* 35, 3362-3367 (1996)); and the Duffy blood-group antigen [RANTES, MCP-1] (Chaudhun, et al., *J. Biol. Chem.,* 269, 7835-7838 (1994)). The β-chemokines include eotaxin, MIP ("macrophage inflammatory protein"), MCP ("monocyte chemoattractant protein") and RANTES ("regulation-upon-activation, normal T expressed and secreted") among other chemokines.

Chemokine receptors, such as CCR-1, CCR-2, CCR-2A, CCR-2B, CCR-3, CCR-4, CCR-5, CXCR-3, CXCR-4, have been implicated as being important mediators of inflammatory and immunoregulatory disorders and diseases, including asthma, rhinitis and allergic diseases, as well as autoimmune pathologies such as rheumatoid arthritis and atherosclerosis. Humans who are homozygous for the 32-basepair deletion in the CCR-5 gene appear to have less susceptibility to rheumatoid arthritis (Gomez, et al., *Arthritis & Rheumatism,* 42, 989-992 (1999)). A review of the role of eosinophils in allergic inflammation is provided by Kita, H., et al., *J. Exp. Med.* 183, 2421-2426 (1996). A general review of the role of chemokines in allergic inflammation is provided by Lustger, A. D., *New England J. Med.,* 338(7), 426-445 (1998).

A subset of chemokines are potent chemoattractants for monocytes and macrophages. The best characterized of these is MCP-1 (monocyte chemoattractant protein-1), whose primary receptor is CCR2. MCP-1 is produced in a variety of cell types in response to inflammatory stimuli in various species, including rodents and humans, and stimulates chemotaxis in monocytes and a subset of lymphocytes. In particular, MCP-1 production correlates with monocyte and macrophage infiltration at inflammatory sites. Deletion of either MCP-1 or CCR2 by homologous recombination in mice results in marked attenuation of monocyte recruitment in response to thioglycollate injection and Listeria monocytogenes infection (Lu et al., *J. Exp. Med.,* 187, 601-608 (1998); Kurihara et al. *J. Exp. Med.,* 186, 1757-1762 (1997); Boring et al. *J. Clin. Invest.,* 100, 2552-2561 (1997); Kuziel et al. *Proc. Natl. Acad. Sci.,* 94, 12053-12058 (1997)). Furthermore, these animals show reduced monocyte infiltration into granulomatous lesions induced by the injection of schistosomal or mycobacterial antigens (Boring et al. *J. Clin. Invest.,* 100, 2552-2561 (1997); Warmington et al. *Am J. Path.,* 154, 1407-1416 (1999)). These data suggest that MCP-1-induced CCR2 activation plays a major role in monocyte recruitment to inflammatory sites, and that antagonism of this activity will produce a sufficient suppression of the immune response to produce therapeutic benefits in immunoinflammatory and autoimmune diseases.

Accordingly, agents which modulate chemokine receptors such as the CCR-2 receptor would be useful in such disorders and diseases.

In addition, the recruitment of monocytes to inflammatory lesions in the vascular wall is a major component of the pathogenesis of atherogenic plaque formation. MCP-1 is produced and secreted by endothelial cells and intimal smooth muscle cells after injury to the vascular wall in hypercholesterolemic conditions. Monocytes recruited to the site of injury infiltrate the vascular wall and differentiate to foam cells in response to the released MCP-1. Several groups have now demonstrated that aortic lesion size, macrophage content and necrosis are attenuated in MCP-1−/− or CCR2−/− mice backcrossed to APO-E −/−, LDL-R −/− or Apo B transgenic mice maintained on high fat diets (Boring et al. *Nature,* 394, 894-897 (1998); Gosling et al. *J. Clin. Invest.,* 103, 773-778 (1999)). Thus, CCR2 antagonists may inhibit atherosclerotic lesion formation and pathological progression by impairing monocyte recruitment and differentiation in the arterial wall.

SUMMARY OF THE INVENTION

The present invention is directed to compounds which are modulators of chemokine receptor activity and are useful in the prevention or treatment of certain inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis. The invention is also directed to pharmaceutical compositions comprising these compounds and the use of these compounds and compositions in the prevention or treatment of such diseases in which chemokine receptors are involved.

DETAILED DESCRIPTION OF THE INVENTION

The present invention is directed to compounds of formula I and formula II:

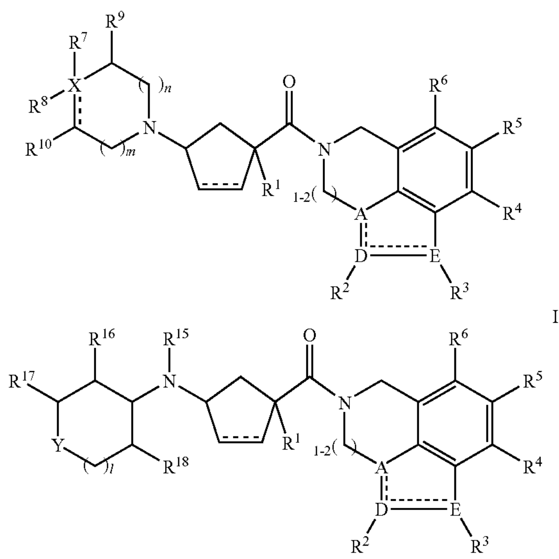

wherein:

A is selected from C or N;

D and E are independently selected from C, N, O, —SO— and —$SO_2$— to make a fused carbocycle (if A, D and E are all C) or a heterocycle (if at least one of A, D, or E is N, O, or S). The dashed lines represent either single or double bonds, where the dashed lines between A-D-E represent either one single and one double bond in either of the 2 possible configurations, or represent 2 single bonds;

X is selected from O, N, S, $SO_2$, or C.

Y is selected from the group consisting of:

—O—, —$NR^{12}$—, —S—, —SO—, —$SO_2$—, and —$CR^{12}R^{12}$—, —$NSO_2R^{14}$—,

—$NCOR^{13}$—, —$CR^{12}COR^{11}$—, —$CR^{12}OCOR^{13}$— and —CO—, where $R^{11}$ is independently selected from: hydroxy, hydrogen, $C_{1-6}$ alkyl, —O—$C_{1-6}$alkyl, benzyl, phenyl and $C_{3-6}$ cycloalkyl, where the alkyl, phenyl, benzyl, and cycloalkyl groups can be unsubstituted or substituted with 1-3 substituents, and where the substituents are independently selected from: halo, hydroxy, $C_{1-3}$alkyl, $C_{1-3}$alkoxy, —$CO_2H$, —$CO_2$—$C_{1-6}$ alkyl, and trifluoromethyl, where $R^{12}$ is selected from: hydrogen, $C_{1-6}$ alkyl, benzyl, phenyl, and $C_{3-6}$ cycloalkyl, where the alkyl, phenyl, benzyl, and cycloalkyl groups can be unsubstituted or substituted with 1-3 substituents, and where the substituents are independently selected from: halo, hydroxy, $C_{1-3}$alkyl, $C_{1-3}$alkoxy, —$CO_2H$, —$CO_2$—$C_{1-6}$ alkyl, and trifluoromethyl, where $R^{13}$ is selected from: hydrogen, $C_{1-6}$ alkyl, —O—$C_{1-6}$alkyl, benzyl, phenyl, $C_{3-6}$ cycloalkyl, where the alkyl, phenyl, benzyl, and cycloalkyl groups can be unsubstituted or substituted with 1-3 substituents, and where the substituents are independently selected from: halo, hydroxy, $C_{1-3}$alkyl, $C_{1-3}$alkoxy, —COH, —$CO_2$—$C_{1-6}$ alkyl, and trifluoromethyl, and where $R^{14}$ is selected from: hydroxy, $C_{1-6}$ alkyl, —O—$C_{1-6}$alkyl, benzyl, phenyl, $C_{3-6}$ cycloalkyl, where the alkyl, phenyl, benzyl, and cycloalkyl groups can be unsubstituted or substituted with 1-3 substituents, and where the substituents are independently selected from: halo, hydroxy, $C_{1-3}$alkyl, $C_{1-3}$alkoxy, —$CO_2H$, —$CO_2$—$C_{1-6}$ alkyl, and trifluoromethyl;

$R^1$ is selected from:

hydrogen, —$C_{1-6}$alkyl, —$C_{0-6}$alkyl-O—$C_{1-6}$alkyl, —$C_{0-6}$alkyl-S—$C_{1-6}$alkyl, —($C_{0-6}$alkyl)-($C_{3-7}$cycloalkyl)-($C_{0-6}$alkyl), hydroxy, heterocycle, —CN, —$NR^{12}R^{12}$, —$NR^{12}COR^{13}$, —$NR^{12}SO_2R^{14}$, —$COR^{11}$, —$CONR^{12}R^{12}$, and phenyl, where the alkyl and the cycloalkyl are unsubstituted or substituted with 1-7 substituents, where the substituents are independently selected from:

(a) halo,
(b) hydroxy,
(c) —O—$C_{1-3}$alkyl,
(d) trifluoromethyl,
(f) $C_{1-3}$alkyl,
(g) —O—$C_{1-3}$alkyl,
(h) —$COR^{11}$,
(i) —$SO_2R^{14}$,
(j) —$NHCOCH_3$,
(k) —$NHSO_2CH_3$,
(l) -heterocycle,
(m) =O, and
(n) —CN, and where the phenyl and heterocycle are unsubstituted or substituted with 1-3 substituents, where the substituents are independently selected from: halo, hydroxy, $C_{1-3}$alkyl, $C_{1-3}$alkoxy and trifluoromethyl;

if D is C, $R^2$ is selected from:

(a) hydrogen,
(b) $C_{1-3}$alkyl, optionally substituted with 1-3 fluoro,
(c) —O—$C_{1-3}$alkyl, optionally substituted with 1-3 fluoro,
(d) hydroxy,
(e) chloro,
(f) fluoro,
(g) bromo, and
(h) phenyl, and
(g) =O (where $R^3$ forms a double bond to E);

if D is N, $R^2$ is selected from:

(a) hydrogen,
(b) $C_{1-3}$alkyl, optionally substituted with 1-3 fluoro,
(c) —O—$C_{1-3}$alkyl, optionally substituted with 1-3 fluoro,
(d) phenyl, and
(e) 0 (to give an N-oxide).

if D is O, SO, or $SO_2$, $R^2$ is nothing;

if E is C, $R^3$ is selected from:

(a) hydrogen, (b) $C_{1-3}$alkyl, optionally substituted with 1-3 fluoro, (c) —O—$C_{1-3}$alkyl, optionally substituted with 1-3 fluoro, (d) hydroxy, (e) chloro, (f) fluoro, (g) bromo, and (h) phenyl, and (g) ═O (where $R^3$ forms a double bond to E);

if E is N, $R^3$ is selected from:

(a) hydrogen, (b) $C_{1-3}$alkyl, optionally substituted with 1-3 fluoro, (c) —O—$C_{1-3}$alkyl, optionally substituted with 1-3 fluoro, (d) phenyl, (e) O (to give an N-oxide).

if E is O, SO, or $SO_2$, $R^3$ is nothing;

$R^4$ is selected from:

(a) hydrogen, (b) $C_{1-3}$alkyl, optionally substituted with 1-3 fluoro, (c) —O—$C_{1-3}$alkyl, optionally substituted with 1-3 fluoro, (d) hydroxy, (e) chloro, (f) fluoro, (g) bromo, and (h) phenyl;

$R_5$ is selected from:

(a) $C_{1-6}$alkyl, where alkyl may be unsubstituted or substituted with 1-6 fluoro and optionally substituted with hydroxyl, (b) —O—$C_{1-6}$alkyl, where alkyl may be unsubstituted or substituted with 1-6 fluoro, (c) —CO—$C_{1-6}$alkyl, where alkyl may be unsubstituted or substituted with 1-6 fluoro, (d) —S—$C_{1-6}$alkyl, where alkyl may be unsubstituted or substituted with 1-6 fluoro, (e) -pyridyl, which may be unsubstituted or substituted with one or more substituents selected from the group consisting of: halo, trifluoromethyl, $C_{1-4}$alkyl, and $COR^{11}$, (f) fluoro, (g) chloro, (h) bromo, (i) —$C_{4-6}$cycloalkyl, (j) —O—$C_{4-6}$cycloalkyl, (k) phenyl, which may be unsubstituted or substituted with one or more substituents selected from the group consisting of: halo, trifluoromethyl, $C_{1-4}$alkyl, and $COR^{11}$, (l) —O-phenyl, which may be unsubstituted or substituted with one or more substituents selected from the group consisting of: halo, trifluoromethyl, $C_{1-4}$alkyl, and $COR^{11}$, (m) —$C_{3-6}$cycloalkyl, where alkyl may be unsubstituted or substituted with 1-6 fluoro, (n) —O—$C_{3-6}$cycloalkyl, where alkyl may be unsubstituted or substituted with 1-6 fluoro, (o)-heterocycle, (p) —CN, and (q) —$COR^{11}$;

$R^6$ is selected from:

(a) hydrogen, (b) alkyl, optionally substituted with 1-3 fluoro, (c) —O—$C_{1-3}$alkyl, optionally substituted with 1-3 fluoro, (d) hydroxy, (e) chloro, (f) fluoro, (g) bromo, and (h) phenyl;

$R^7$ is selected from:

hydrogen, ($C_{0-6}$alkyl)-phenyl, ($C_{0-6}$alkyl)-heterocycle, ($C_{0-6}$alkyl)-$C_{3-7}$cycloalkyl, ($C_{0-6}$alkyl)-$COR^{11}$, ($C_{0-6}$alkyl)-(alkene)-$COR^{11}$, ($C_{0-6}$alkyl)-$SO_3H$, ($C_{0-6}$alkyl)-W—$C_{0-4}$alkyl, ($C_{0\ 6}$alkyl)-$CONR^{12}$-phenyl, ($C_{0-6}$alkyl)-$CONR^{20}$—V—$COR^{11}$, and nothing (when X is O, S, or $SO_2$), where V is selected from $C_{1-6}$alkyl or phenyl, and where W is selected from: a single bond, —O—, —S—, —SO—, —$SO_2$—, —CO—, —$CO_2$—, —$CONR^{12}$— and —$NR^{12}$—, where the $R^{20}$ can be hydrogen, $C_{1-4}$alkyl, or where $R^{20}$ is joined via a 1-5 carbon tether to one of the carbons of V to form a ring, where the $C_{0-6}$alkyl is unsubstituted or substituted with 1-5 substituents, where the substituents are independently selected from:

(a) halo, (b) hydroxy, (c) —$C_{0-6}$alkyl (d) —O—$C_{1-3}$alkyl, (e) trifluoromethyl, and (f) —$C_{0-2}$alkyl-phenyl, where the phenyl, heterocycle, cycloalkyl, and $C_{0-4}$alkyl is unsubstituted or substituted with 1-5 substituents where the substituents are independently selected from:

(a) halo, (b) trifluoromethyl, (c) hydroxy, (d) $C_{1-3}$alkyl, (e) —O—$C_{1-3}$alkyl, (f) —$C_{0-3}$—$COR^{11}$, (g) —CN, (h) —$NR^{12}R^{12}$, (i) —$CONR^{12}R^{12}$, and (j) —$C_{0-3}$-heterocycle, or where the phenyl and heterocycle may be fused to another heterocycle, which itself may be unsubstituted or substituted with 1-2 substituents independently selected from hydroxy, halo, —COR11, and —$C_{1-3}$alkyl, and where alkene is unsubstituted or substituted with 1-3 substituents which are independently selected from:

(a) halo, (b) trifluoromethyl, (c) $C_{1-3}$alkyl, (d) phenyl, and (e) heterocycle;

$R^8$ is selected from:

(a) hydrogen, (b) nothing when X is either O, S, $SO_2$ or N or when a double bond joins the carbons to which $R^7$ and $R^{10}$ are attached, (c) hydroxy, (d) $C_{1-6}$alkyl, (e) $C_{1-6}$alkyl-hydroxy, (f) —O—$C_{1-3}$alkyl, (g) —$COR^{11}$, (h) —$CONR^{12}R^{12}$, and (i) —CN;

or where $R^7$ and $R^8$ may be joined together to form a ring which is selected from:

(a) 1H-indene, (b) 2,3-dihydro-1H-indene, (c) 2,3-dihydro-benzofuran, (d) 1,3-dihydro-isobenzofuran,
(e) 2,3-dihydro-benzothiofuran,
(f) 1,3-dihydro-isobenzothiofuran,
(g) 6H-cyclopenta[d]isoxazol-3-ol
(h) cyclopentane, and
(i) cyclohexane, where the ring formed may be unsubstituted or substituted with 1-5 substituents independently selected from:

(a) halo,
(b) trifluoromethyl,
(c) hydroxy,
(d) $C_{1-3}$alkyl,
(e) —O—$C_{1-3}$alkyl,
(f) —$C_{0-3}$—$COR^{11}$,
(g) —CN,
(h) —$NR^{12}R^{12}$,
(i) —$CONR^{12}R^{12}$, and
(j) —$C_{0-3}$-heterocycle, or where $R^7$ and $R^9$ or $R^8$ and $R^{10}$ may be joined together to form a ring which is phenyl or heterocycle, wherein the ring is unsubstituted or substituted with 1-7 substituents where the substituents are independently selected from:

(a) halo,
(b) trifluoromethyl,
(c) hydroxy,
(d) $C_{1-3}$alkyl,
(e) —O—$C_{1-3}$alkyl,
(f) —$COR^{11}$,
(g) —CN,
(h) —$NR^{12}R^{12}$, and
(i) —$CONR^{12}R^{12}$;

$R^9$ and $R^{10}$ are independently selected from:

(a) hydrogen,
(b) hydroxy,
(c) $C_{1-6}$alkyl,
(d) $C_{1-6}$alkyl-$COR^{11}$,
(e) $C_{1-6}$alkyl-hydroxy,
(f) —O—$C_{1-3}$alkyl,
(g) =O, when $R^9$ or $R^{10}$ is connected to the ring via a double bond
(h) halo;

$R^{15}$ is selected from:

(a) hydrogen, and
(b) $C_{1-6}$alkyl, which is unsubstituted or substituted with 1-3 substituents where the substituents are independently selected from: halo, hydroxy, —$CO_2H$, —$CO_2C_{1-6}$alkyl, and —O—$C_{1-3}$alkyl;

$R^{16}$ is selected from:

(a) hydrogen,
(b) $C_{1-6}$alkyl, where alkyl may be unsubstituted or substituted with 1-6 substituents where the substituents are chosen from the group: fluoro, $C_{1-3}$alkoxy, hydroxy, —$COR^{11}$,
(c) fluoro,
(d) —O—$C_{1-3}$alkyl, where alkyl may be unsubstituted or substituted with 1-3 fluoro, and
(e) $C_{3-6}$ cycloalkyl,
(f) —O—$C_{3-6}$cycloalkyl,
(g) hydroxy,
(h) —$COR^{11}$, and
(i) —$OCOR^{13}$, or $R^{15}$ and $R^{16}$ may be joined together via a $C_{2-4}$alkyl or a $C_{0-2}$alkyl-O—$C_{1-3}$alkyl chain to form a 5-7 membered ring;

$R^{17}$ is selected from:

(a) hydrogen,
(b) $C_{1-6}$alkyl, where alkyl may be unsubstituted or substituted with 1-6 substituents where the substituents are chosen from the group: fluoro, $C_{1-3}$alkoxy, hydroxy, —$COR^{11}$,
(c) $COR^{11}$,
(d) hydroxy, and
(e) —O—$C_{1-6}$alkyl, where alkyl may be unsubstituted or substituted with 1-6 substituents where the substituents are chosen from the group: fluoro, $C_{1-3}$alkoxy, hydroxy, and —$COR^{11}$, or $R^{16}$ and $R^{17}$ may be joined together by a $C_{1-4}$alkyl chain or a $C_{0-3}$alkyl-O—$C_{0-3}$alkyl chain to form a 3-6 membered ring;

$R^{18}$ is selected from:

(a) hydrogen,
(b) $C_{1-6}$alkyl, where alkyl may be unsubstituted or substituted with 1-6 fluoro,
(c) fluoro,
(d) —O—$C_{3-6}$cycloalkyl, and
(e) —O—$C_{1-3}$alkyl, where alkyl may be unsubstituted or substituted with 1-6 fluoro, or $R^{16}$ and $R^{18}$ may be joined together by a $C_{2-3}$alkyl chain to form a 5-6 membered ring, where the alkyl are unsubstituted or substituted with 1-3 substituents where the substiuents are independently selected from: halo, hydroxy, —$COR^{11}$, $C_{1-3}$alkyl, and $C_{1-3}$alkoxy, or $R^{16}$ and $R^{18}$ may be joined together by a $C_{1-2}$alkyl-O—$C_{1-2}$alkyl chain to form a 6-8 membered ring, where the alkyl are unsubstituted or substituted with 1-3 substituents where the substiuents are independently selected from: halo, hydroxy, —$COR^{11}$, $C_{1-3}$alkyl, and $C_{1-3}$alkoxy, or $R^{16}$ and $R^{18}$ may be joined together by a —O—$C_{1-2}$alkyl-O-chain to form a 6-7 membered ring, where the alkyl are unsubstituted or substituted with 1-3 substituents where the substiuents are independently selected from: halo, hydroxy, —$COR^{11}$ $C_{1-3}$alkyl, and $C_{1-3}$alkoxy;

$R^{19}$ selected from:

(a) hydrogen,
(b) phenyl, and
(c) $C_{1-6}$alkyl which may be substituted or unsubstituted with 1-6 of the following substituents: —$COR^{11}$, hydroxy, fluoro, chloro and —O—$C_{1-3}$alkyl;

l, m, and n are each selected from 0, 1 and 2.

and pharmaceutically acceptable salts thereof and individual diastereomers thereof.

Compounds of the present invention include those of formula Ia:

Ia

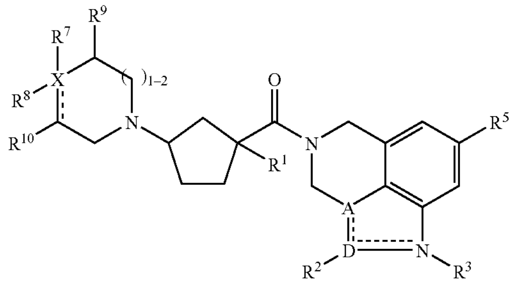

Wherein D, A, R1, R2, R3, R5, R7, R8, R9, R10 and X are defined herein.

Compounds of the present invention also include those of formula IIa:

IIa

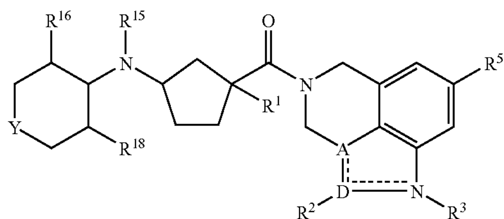

wherein D, A, R1, R2, R3, R5, R15, R16, R18 and X are defined herein.

Further, compounds of the present invention include those of formula Ib:

Ib

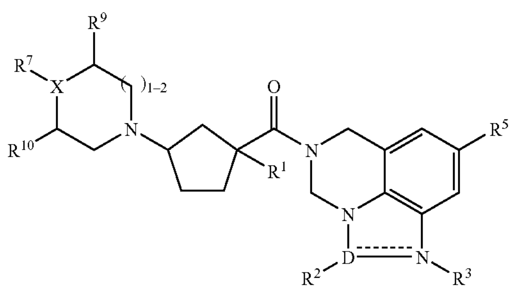

wherein D, R1, R2, R3, R5, R7, R9, R10 and X are defined herein.

Further still, compounds of the present invention also include those of formula IIb:

IIb

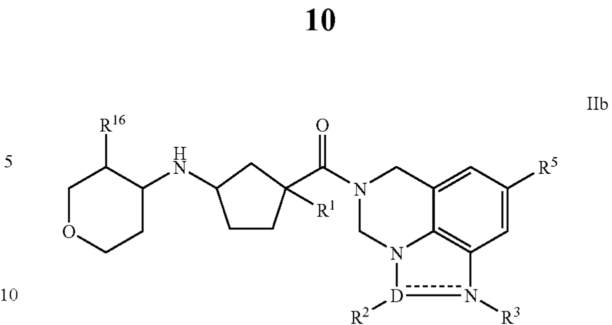

wherein D, R1, R2, R3, R5, R16, and X are defined herein.

In the present invention it is preferred that X is C, O or N.

In the present invention it is more preferred that X is C or O.

In the present invention it is preferred that Y is —$CH_2$— or —O—.

In the present invention it is more preferred that A is N.

In the present invention it is preferred that E is N.

In the present invention it is preferred that D is selected from C, N, and $SO_2$.

In the present invention it is preferred that $R^1$ is selected from:

—$C_{1-6}$alkyl, —$C_{0-6}$alkyl-O—$C_{1-6}$alkyl, and —($C_{0-6}$alkyl)-($C_{3-7}$cycloalkyl)-($C_{0-6}$alkyl), where the alkyl and the cycloalkyl are unsubstituted or substituted with 1-7 substituents where the substituents are independently selected from:

(a) halo,
(b) hydroxy,
(c) —O—$C_{1-3}$alkyl,
(d) trifluoromethyl,
(f) $C_{1-3}$alkyl,
(g) —O—$C_{1-3}$alkyl,
(h) —$COR^{11}$,
(i) —CN,
(j) —$NR^{12}R^{12}$, and
(k) —$CONR^{12}R^{12}$.

In the present invention it is more preferred that $R^1$ is selected from:

(1) —$C_{1-6}$alkyl, which is unsubstituted or substituted with 1-6 substituents where the substituents are independently selected from:
(a) halo,
(b) hydroxy,
(c) —O—$C_{1-3}$alkyl,
(d) trifluoromethyl, and
(e) —$COR^{11}$, (2) —$C_{0-6}$alkyl-O—$C_{1-6}$alkyl-, which is unsubstituted or substituted with 1-6 substituents where the substituents are independently selected from:
(a) halo,
(b) trifluoromethyl, and
(c) —$COR^{11}$, and (3) —($C_{3-5}$cycloalkyl)-($C_{0-6}$alkyl), which is unsubstituted or substituted with 1-7 substituents where the substituents are independently selected from:
(a) halo,
(b) hydroxy,
(c) —O—$C_{1-3}$alkyl,
(d) trifluoromethyl, and
(e) —$COR^{11}$.

In the present invention it is still more preferred that $R^1$ is selected from:

(a) $C_{1-6}$alkyl,
(b) $C_{1-6}$alkyl substituted with hydroxy
(c) $C_{1-6}$alkyl substituted with 1-6 fluoro.

In the present invention it is most preferred that $R^1$ is selected from:

(a) —$CH(CH_3)_2$, (b) —$CH(OH)CH_3$, and (c) —$CH_2CF_3$.

In the present invention it is preferred that when D is C, $R^2$ is hydrogen or is oxygen (hydroxy when a bond joining D and E or joining D and A is a double bond; or oxo (where $R^2$ is joined to D via double bond) when the bond joining D and E or joining D and A is a single bond).

In the present invention it is preferred that when D is N, $R^2$ is hydrogen or is nothing, depending upon the bond order of the D-E and A-D bonds.

In the present invention when it is preferred that $R^3$ is hydrogen or methyl.

In the present invention it is preferred that $R^4$ is hydrogen.

In the present invention it is preferred that $R^5$ is selected from:

(a) $C_{1-6}$alkyl substituted with 1-6 fluoro, (b) —O—$C_{1-6}$alkyl substituted with 1-6 fluoro, (c) chloro, (d) bromo, and (e) phenyl.

In the present invention it is more preferred that $R^5$ is selected from:

(a) trifluoromethyl, (b) trifluoromethoxy, (c) chloro, (d) bromo, and (e) phenyl.

In the present invention it is most preferred that $R^5$ is trifluoromethyl.

In the present invention it is preferred that $R^6$ is hydrogen.

In the present invention it is preferred, when X is C or N, that $R^7$ is phenyl, heterocycle, $C_{3-7}$cycloalkyl, $C_{1-6}$alkyl, —$COR^{11}$, and —CONH—V—$COR^{11}$, where V is selected from $C_{1-6}$alkyl or phenyl, and where the phenyl, heterocycle, $C_{3-7}$cycloalkyl, and $C_{1-6}$alkyl is unsubstituted or substituted with 1-5 substituents where the substituents are independently selected from:

(a) halo, (b) trifluoromethyl, (c) hydroxy, (d) $C_{1-3}$alkyl, (e) —O—$C_{1-3}$alkyl, (f) —$COR^{11}$, (g) —CN, (h) -heterocycle, and (i) —$CONR^{12}R^{12}$.

In the present invention it is more preferred that $R^7$ is phenyl, heterocycle, $C_{1-4}$alkyl, —$COR^{11}$, and —CONH—V—$COR^{11}$, where V is selected from $C_{1-6}$alkyl or phenyl, and where the phenyl, heterocycle, and $C_{1-4}$alkyl is unsubstituted or substituted with 1-3 substituents where the substituents are independently selected from:

(a) halo, (b) hydroxy, (c) $C_{1-3}$alkyl, (d) —O—$C_{1-3}$alkyl, (e) —$COR^{11}$, and (f) -heterocycle In the present invention it is preferred that when X is C, $R^8$ is hydrogen;

In the present invention it is preferred that $R^9$ and $R^{10}$ are selected from:

(a) hydrogen, (b) hydroxy, (c) —$CH_3$, (d) —O—$CH_3$, and (e) =O (where $R^9$ is joined to the ring via a double bond).

In the present invention it is preferred that $R^{15}$ is hydrogen or methyl.

In the present invention it is preferred that $R^{16}$ is selected from:

(a) hydrogen, (b) $C_{1-3}$alkyl, which is unsubstituted or substituted with 1-6 fluoro, (c) —O—$C_{1-3}$alkyl, and (d) fluoro, and (e) hydroxy.

In the present invention it is more preferred that $R^{16}$ is selected from:

(a) hydrogen, (d) trifluoromethyl, (c) methyl, (d) methoxy, (e) ethoxy, (f) ethyl, (g) fluoro, and (h) hydroxy.

In the present invention it is preferred that $R^{17}$ is hydrogen.

In the present invention it is preferred that $R^{18}$ is selected from:

(a) hydrogen, (b) methyl, and (c) methoxy.

In the present invention it is preferred that $R^{18}$ is hydrogen.

In the present invention it is also preferred that $R^{16}$ and $R^{18}$ are joined together by a —$CH_2CH_2$— chain or a —$CH_2CH_2CH_2$— chain to form a cyclopentyl ring or a cyclohexyl ring.

In the present invention it is preferred that m=1 or 2.

In the present invention it is preferred that l=1.

In the present invention it is preferred that n=1 or 2.

and pharmaceutically acceptable salts and stereoisomers thereof.

Several methods for preparing the compounds of this invention are illustrated in the following Schemes and Examples. Starting materials are made by known procedures or as illustrated.

SCHEME 1

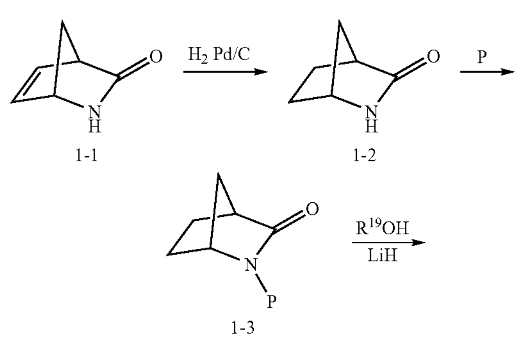

-continued

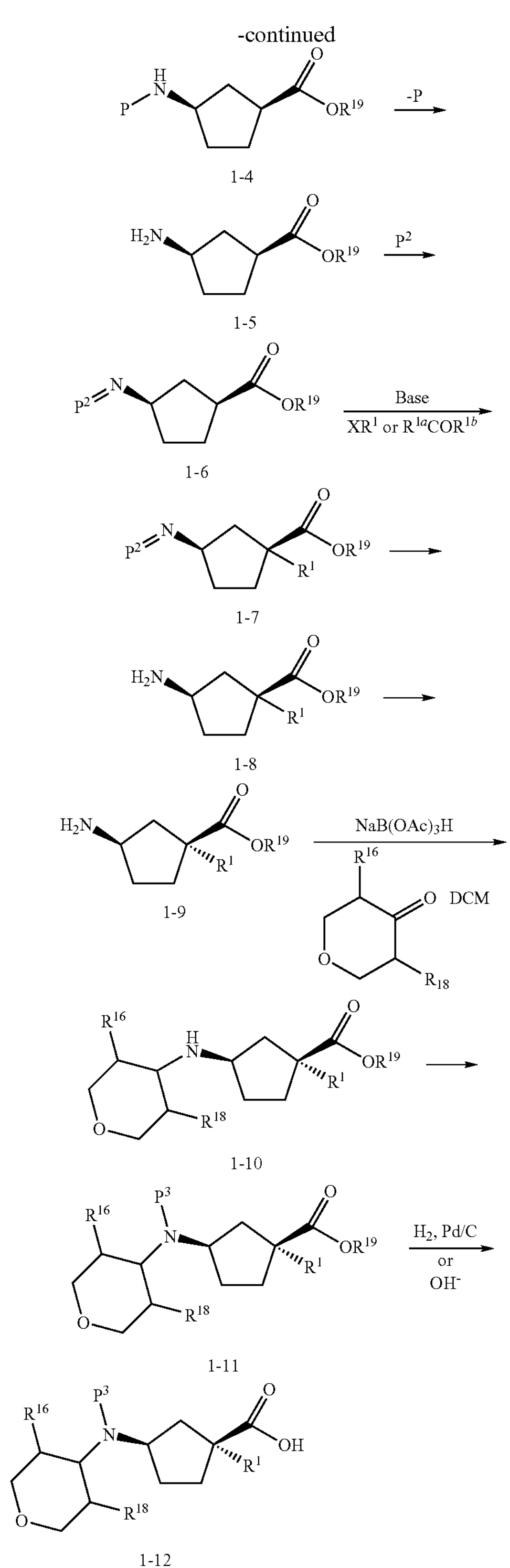

The preparation of carboxylic acids 1-12 to be used as an intermediates in the preparation of the invention is described in scheme 1. Hydrogenation of commercially available (−)-2-azabicyclo[2,2,1]hept-5-en-3-one 1-1 followed by protection of the amine with protecting group P (i.e. BOC, Cbz) and subsequent lithium hydride catalyzed ring opening, in the presence of alcohols (where $R^{19}$=Bn, Me, etc) yields the ester 1-4. Replacement of an acid labile protecting group $P^1$ with a more base stable imine protecting group $P^2$ (i.e. diphenylmethylimine), followed by alkylation with an alkyl halide or aldehyde or ketone yields imine 1-7, which after hydrolysis is purified to a single diastereomer 1-9. Reductive amination of 1-9, with a tetrahydropyranone intermediate is followed by protection of the amine with an acid stable, base labile protecting group ($P^3$)(i.e. trifluoroacetate) gives ester 1-11 which upon hydrolysis or hydrogenolysis gives the intermediate acid 1-12.

SCHEME 1A

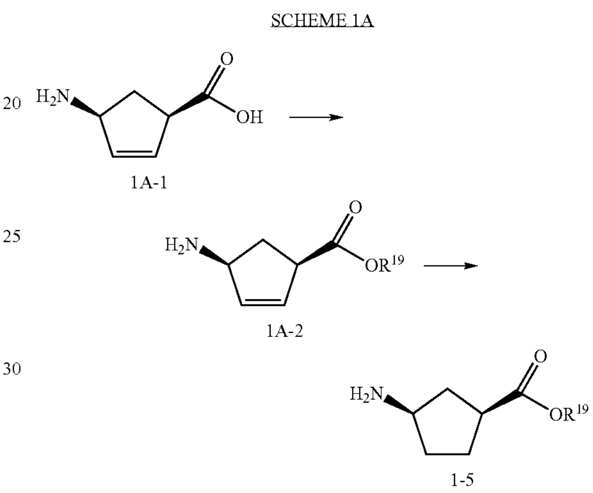

Scheme 1A shows an alternate route to Intermediate 1-5. Esterification of the commercially available acid 1A-1 followed by catalytic hydrogenation of the olefin 1A-2 gives 1-5 in high yield.

SCHEME 1B

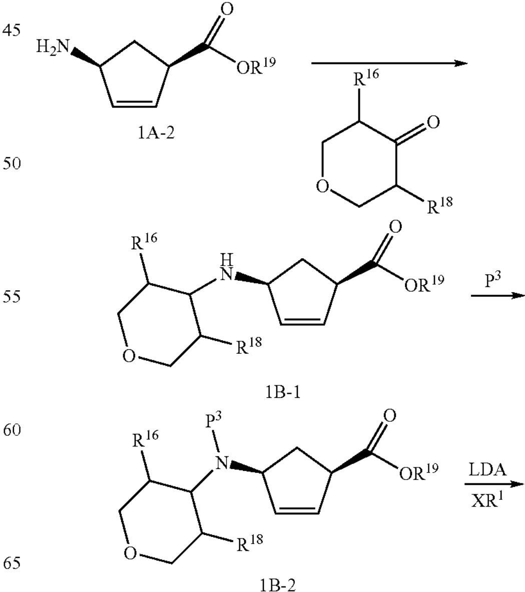

-continued

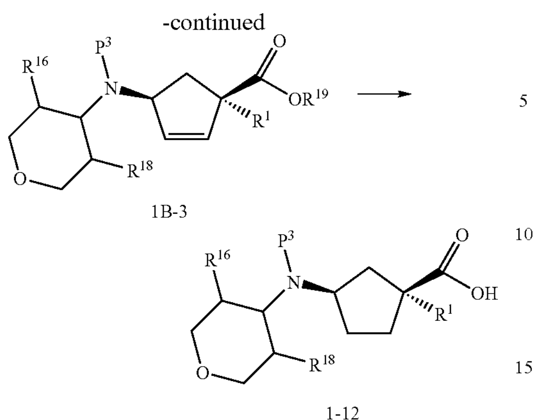

Carboxylic acid 1-12 can also be prepared by the direct assymetric alkylation of the unsaturated intermediate 1B-2 to give intermediate 1B-3. If a hydrogenolizable ester is used (such as Bn), this can be converted in one step to intermediate 1-12. Intermediate 1B-2 is directly prepared from intermedaite 1A-2 by a reductive amination with the tetrahydropyranone followed by protection of the amine with $P^3$ as detailed in Scheme 1.

SCHEME 2

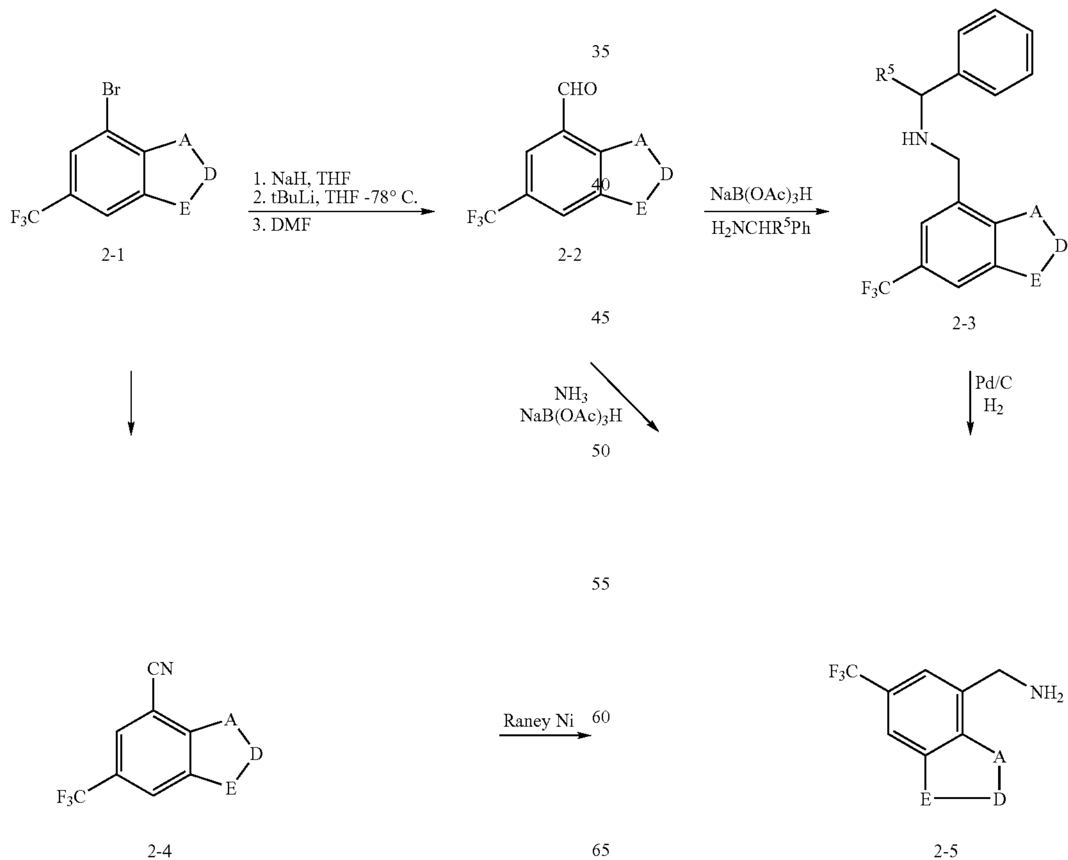

Amine components 2-5 to be used as intermediates in the said invention can be prepared according to Scheme 2. Bromides 2-1 are either commercially available or prepared in one step according to literature procedures. Conversion to the methyl amine 2-5 can be achieved by formylation to 2-2 followed by either a direct reductive amination with ammonia or indirectly through benzylamines of the structure 2-3 which are much more easily purified. Conversely 2-5 can be prepared by reduction of nitrites 24, prepared in one step using palladium (0) chemistry.

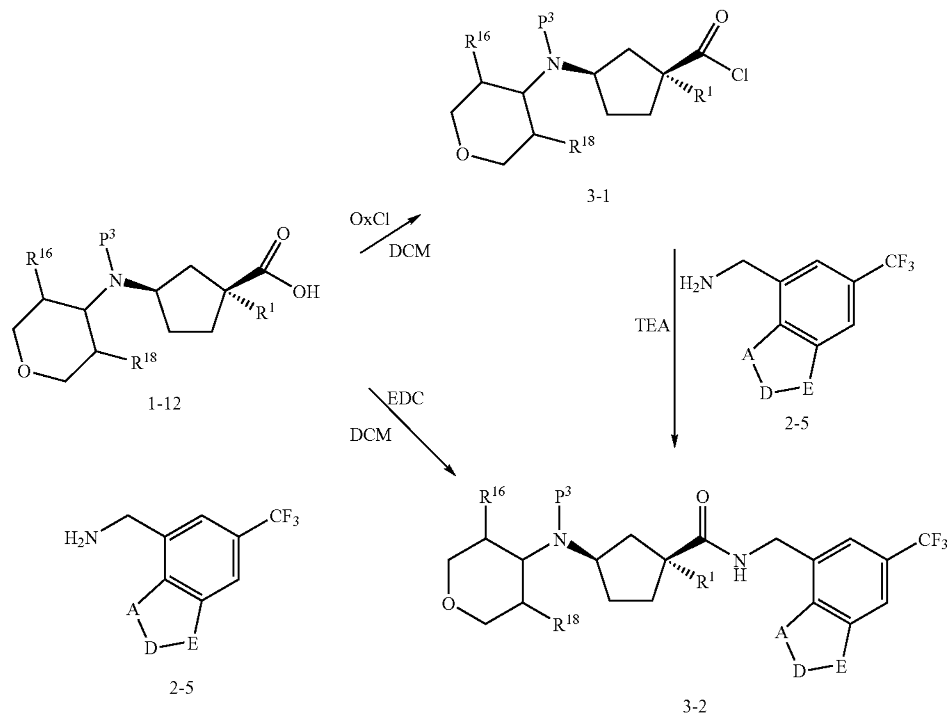

Amine components 2-5 can be coupled to acids 1-12 directly using EDC or indirectly through acid chlorides 3-1 to give intermediates of the form 3-2.

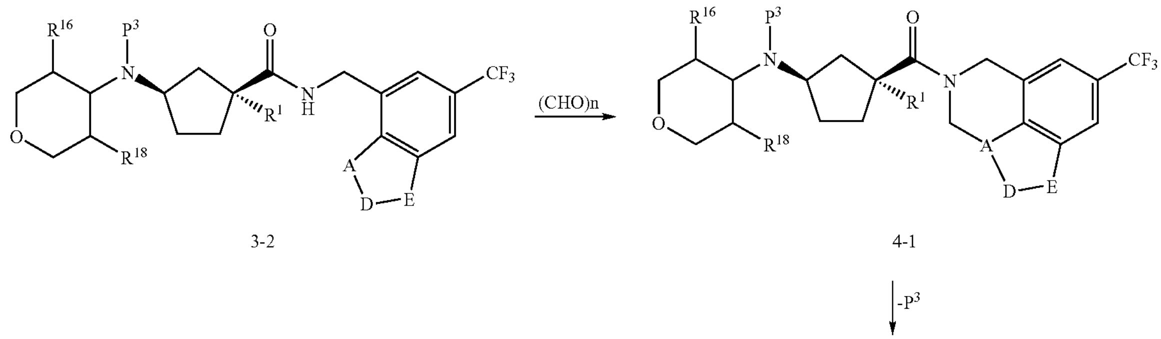

-continued

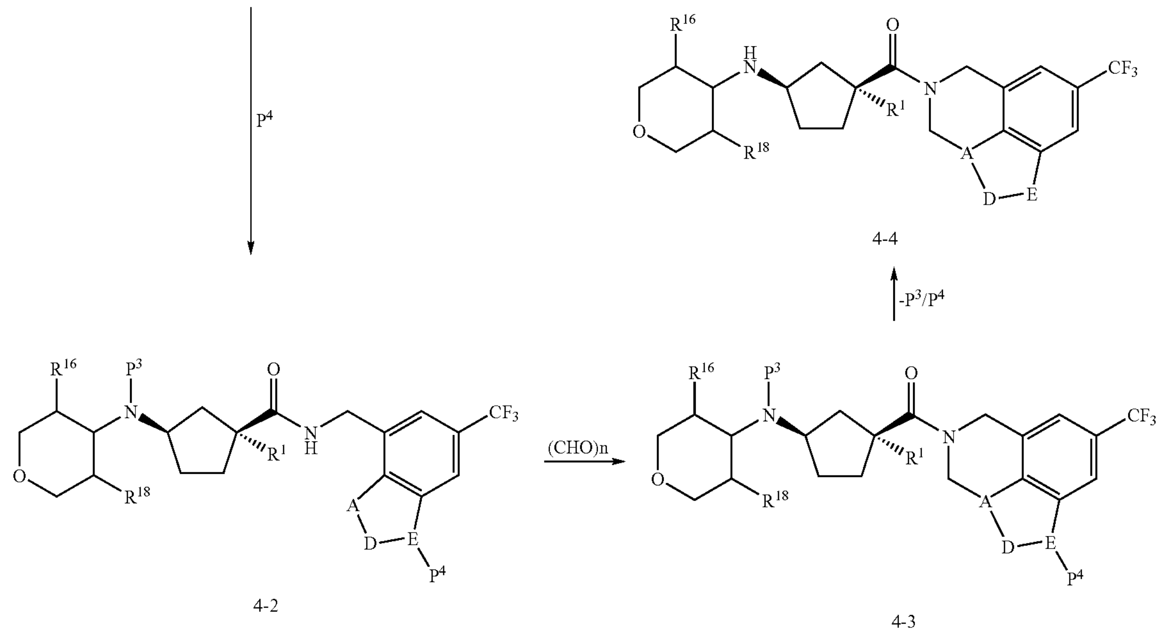

The preparation of chemokine modulators 4-4 within the scope of the invention are shown in Scheme 4. Cyclization of 3-2 can be achieved directly with paraformaldehyde in toluene to give 4-1 which upon deprotection gives 4-4. Some cases required the protection of atom Z with acid stable protecting groups $P^4$ (i.e. Cbz, BOC, Alloc) to give 42 before the cyclization to 4-3 can be achieved.

Z-alkylated products of the structure 5-1 are prepared directly from intermediate 3-2 by alkylation with alkyl halides. Cyclization with paraformaldehyde followed by the removal of the $P^3$ protecting group gives final compounds of the form 5-3.

SCHEME 5

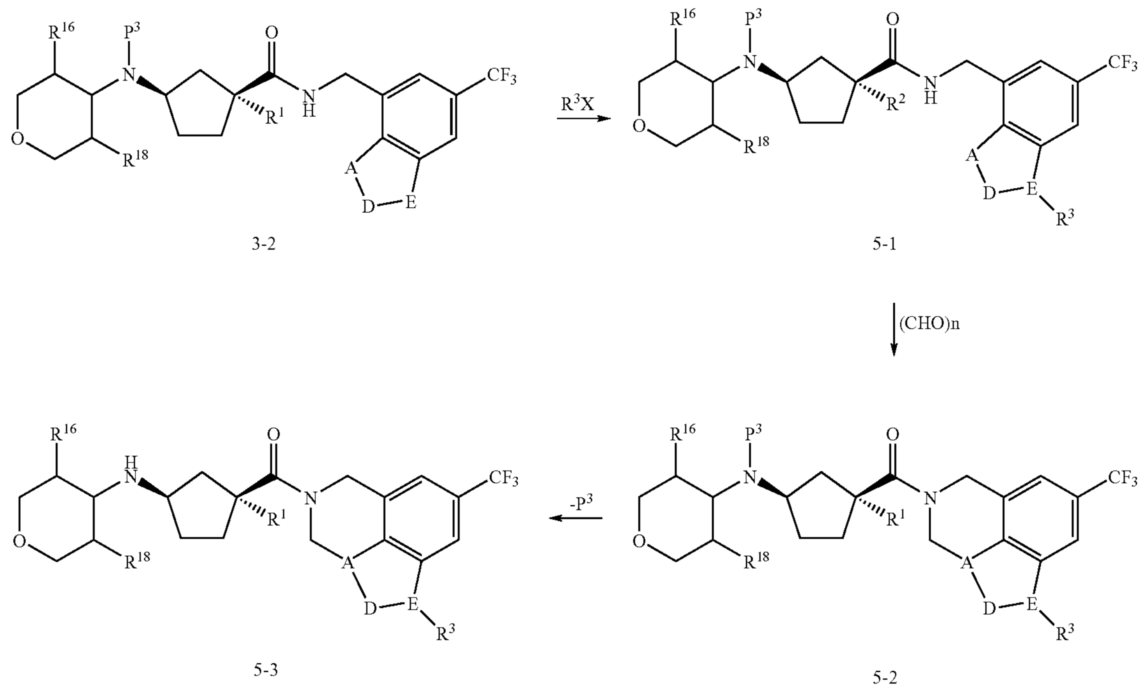

SCHEME 6

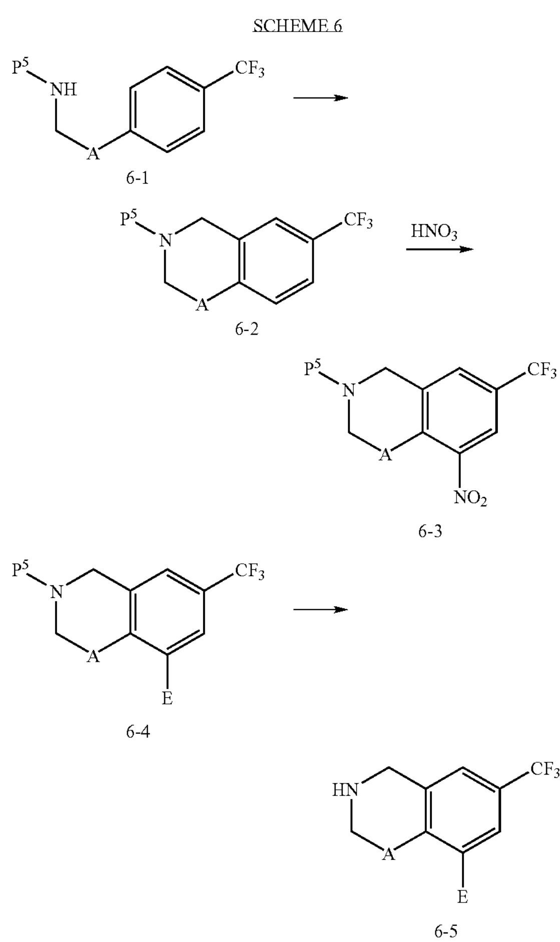

-continued

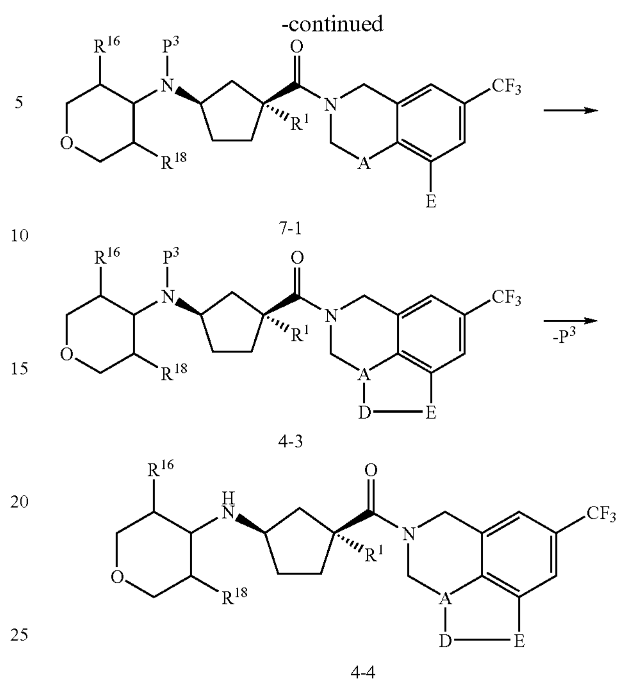

In the case where Y is carbon, compounds of the structure 6-5 can be synthesized by direct reduction of the nitro compound 6-3 (where Z is N) or by diazotization and replacement of the reduced intermediate (to get Z=O), followed by the removal of the acid stable protecting group $P^5$. 6-3 can be readily synthesized by nitration of 6-2 which in turn can be easily prepared by known methods from 6-1.

SCHEME 7

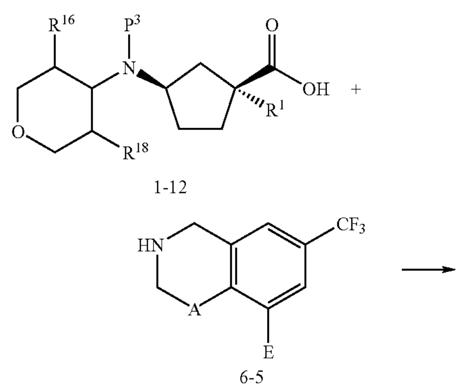

Products of the form 4-4 can alternatively be directly prepared from intermediates 7-1, which are prepared by the direct coupling of 6-5 with 1-12 by the methods described in Scheme 3.

Procedures for the production of certain intermediates useful in synthesizing the compounds of this invention are described below.

INTERMEDIATE 1

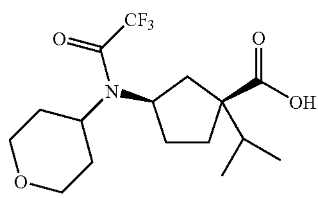

Procedure 1-A:

Step A:

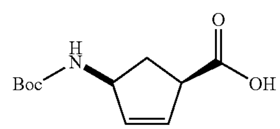

A mixture of (1R,4S)-4-amino-cyclopen-2-ene carboxylic acid (130 g, 1.0 mol), water (250 mL), sodium bicarbonate (170 g, 2.0 mol) and THF (750 mL) was stirred for 30 min, then solid di-tert-butyl dicarbonate (230 g, 1.05 mol) was added. The mixture was stirred over the weekend, filtered to remove the insoluble material, evaporated to remove the THF, and cooled to 0° C. To the residue was added 2 N aqueous HCl (~500 mL) until pH=3. The resulting precipitate was collected by filtration and washed with water, and dried under vacuum overnight. The desired acid was obtained as a white solid (230 g, 100%).

$^1$H NMR (400 MHz, $CD_3OD$): δ 5.95 (m, 1H), 5.79 (m, 1H), 4.80 (br s, 1H), 3.45 (m, 1H), 2.50 (m, 1H), 1.79 (m, 1H), 1.44 (s, 9H).

Step B:

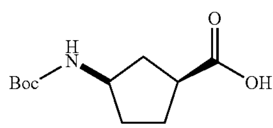

The acid prepared in Step A (230 g, 1.0 mol) and 10% Pd/C (5.0 g) in 500 mL of methanol on a Parr shaker was hydrogenated under 50 psi of hydrogen for 1 h. The catalyst was removed by filtration and the filtrate was evaporated. The residue was dissolved in dichloromethane and dried over anhydrous sodium sulfate. After filtration, the filtrate was evaporated and dried under vacuum. The title compound was obtained as a light yellow solid (230 g, 99%). LC-MS for C11H19NO4 [$M^+H^+$] calculated 230, found 230.

Step C:

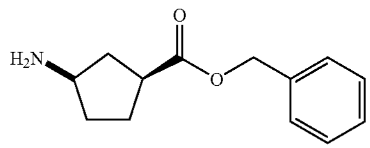

To a mechanically stirred solution of the acid (Step B, Procedure 1-A, Intermediate 1) (230 g, 1.0 mol) in 500 mL of DMF was added solid potassium carbonate (210 g, 1.5 mol). The resulting mixture was stirred for 20 minutes, a neat benzyl bromide (120 mL, 1.0 mol) was added in one portion. An exothermic reaction was observed. After stirred for 3 h at room temperature, the entire mixture was dumped into an ice-water mixture (1000 mL). The crude product was extracted out with ether (2×800 mL). The combined ether layers were washed with water, dried over sodium sulfate, filtered and evaporated to offer a yellow solid. This solid was mixed with 4 N HCl in dioxane (400 mL), stirred overnight and condensed. The resulting solid was collected by filtration, washed with ether and dried under vacuum. The title product was obtained as a hydrochloride salt (140 g, 55%). $^1$H NMR (400 MHz, $CD_3OD$): δ 5.15 (s, 2H), 3.65 (m, 1H), 3.02 (q, J=8 Hz, 1H), 2.50 (m, 1H), 2.15 (m, 1H), 2.05 (m, 2H), 1.90 (m, 1H), 1.75 (m, 1H).

Step D:

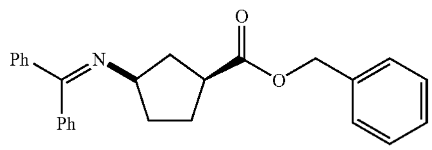

The amino benzyl ester HCl salt (Step C, Procedure 1-A, Intermediate 1)(130 g, 0.50 mol) was suspended in 500 mL of dichloromethane. Benzophenone imine (91 g, 0.50 mol) was added. The resulting mixture was stirred overnight, and filtered to remove the inorganic salt. The filtrate was washed with water and brine, dried over sodium sulfate, and evaporated. The residue was dissolved in 200 mL of toluene, and evaporated. This procedure was repeated once more. The title compound (178 g) was obtained as a brown oil which was used in the next step without further purification. $^1$H NMR (400 MHz, $CDCl_3$): δ 1.80 (m, 1H), 1.95 (m, 2H), 2.15 (m, 2H), 2.50 (m, 1H), 2.89 (m, 1H), 3.61 (m, 1H), 5.20 (s, 2H), 7.18 (d, 2H), 7.38 (m, 8H), 7.47 (m, 3H), 7.64 (d, 2H).

Step E:

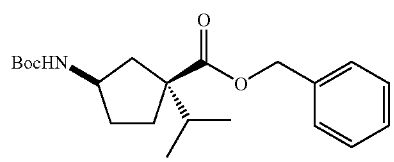

The starting Schiff base benzyl ester (Step D, Procedure 1-A, Intermediate 1)(76.6 g, 200 mmol) in 300 mL of THF was cooled to −78° C. under nitrogen. While stirring, a solution of LDA (2.0 M, 110 mL, 220 mmol) in heptane was added over 20 minutes. The mixture was stirred for 30 minutes at −78° C., then a solution of 68 mL of isopropyl iodide (440 mmol) in 50 mL of THF was added, and the mixture was allowed to stir for 30 min. The reaction temperature was raised to 0° C. by removing the cooling bath. After being stirred for 2 h, the entire mixture was evaporated to remove the THF. The residue was dissolved in ether (1000 mL), washed with water and brine, dried over sodium sulfate, and evaporated. The crude product was dissolved in 500 mL of THF, mixed with 400 mL of aqueous 1 N HCl, stirred for 1 h, and evaporated to remove THF at 50° C. The aq. solution was extracted with hexane (3×), made alkaline with saturated aqueous sodium carbonate (pH>9), mixed and stirred with a solution of di-tert-butyl dicarbonate (53 g) in 500 mL of dichloromethane for 30 min. The organic phase was separated and the aqueous phase was extracted with dichloromethane (3×). The combined organic phases were dried over sodium sulfate and evaporated. The residue was purified by flash chromatography (silica gel, 10% EtOAc/hexane) to yield a mixture of the title compound as a mixture of cis and trans isomers (~1:1, 24 g). Further purification on MPLC (8% EtOAc/Hexane) afforded the single desired cis isomer (fast-eluted, 7.3 g) and the undesired trans isomer (slow-eluted). ESI-MS calc. for C21H31NO4: 361; Found: 362 (M+H). $^1$H NMR (500 MHz, $CDCl_3$): δ 7.36 (m, 5H), 5.14 (s, 2H), 4.77 (m, 1H), 4.01 (d, J=5.0 Hz, 1H), 2.17 (m, 1H), 1.99-1.53 (m, 5H), 1.42 (m, 9H), 0.85 (d, J=7.0 Hz, 6H).

Step F:

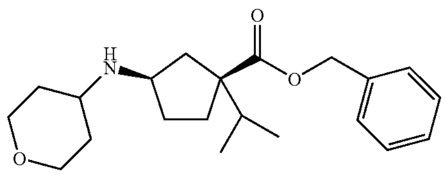

The BOC-amine from Step E (7.3 g, 21 mmol) was treated with hydrogen chloride (4 N solution in dioxane). The reaction was allowed to stir for 1.5 h at room temperature before being concentrated to remove the dioxane. The resultant solid was dissolved in DCM (150 mL) and treated with tetrahydropyranone (2.4 g, 24 mmol) and triethylamine (2.8 mL, 20 mmol). The resulting solution was stirred at room temperature for 5 min before 4 Å powdered molecular sieves (~5 g) and sodium triacetoxyborohydride (17 g, 80 mmol) where added. The mixture was stirred for 2 h at room temperature. The reaction was filtered through celite and washed with a saturated aqueous sodium bicarbonate solution then brine. The organic layer was dried over $MgSO_4$, filtered, and concentrated under reduced pressure. To give 6.7 g of a colorless oil (97%). ESI-MS calc. for C21H31NO3: 345; Found: 346 (M+H).

Step G:

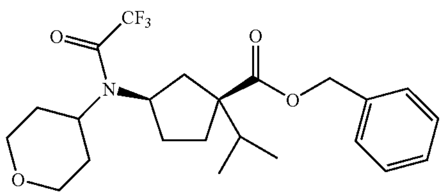

The amine from Step F (6.6 g, 19 mmol) was added to a solution of DCM (100 mL) and triethylamine (2.9 mL, 21 mmol). Trifluoroacetic anhydride (3.0 mL, 21 mmol) was added to the solution dropwise at room temperature and the resulting solution was allowed to stir at room temperature for 2.5 h. The reaction was diluted with DCM (100 mL) and washed with hydrochloric acid (1 N aqueous solution) followed by brine. The organic layer was dried over $MgSO_4$, filtered and concentrated under reduced pressure. The crude yellow oil was purified by MPLC (silica gel, 0 to 30% EA/Hexanes) to give 4.9 g of a colorless oil (58%). $^1$H NMR ($CDCl_3$, 500 MHz): δ 7.37 (m, 5M), 5.18 (m, 2H), 4.20-3.88 (m, 4H), 3.64 (m, 1H), 3.42 (t, J=12.0 Hz, 1H), 3.26 (t, J=11.5 Hz, 1H), 3.18 (t, J=11.5 Hz, 1H), 2.81-2.65 (m, 2H), 2.26 (m, 1H), 1.89-1.80 (m, 3H), 1.64-1.40 (m, 3H), 0.874 (m, 6H).

Step H:

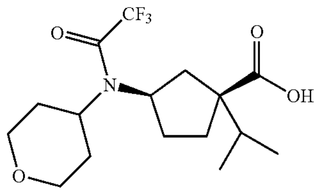

The product from Step G (3.5 g, 7.9 mmol) was dissolved in methanol (60 mL) and treated with 20% palladium hydroxide on activated carbon (350 mg). This mixture was placed under a hydrogen atmosphere (1 atm) and allowed to stir at room temperature for 1.2 h. the reaction was filtered through celite and concentrated under reduced pressure to give 2.63 g of a white solid (95%).

Procedure 1-B:

Step A:

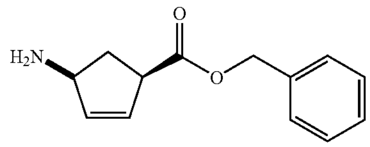

To a magnetically stirred solution of the acid (Step A, Procedure 1-A, Intermediate 1) (159 g, 700 mmol) in 500 mL of DMF was added solid potassium carbonate (138 g, 1.00 mol). The resulting mixture was stirred for 20 minutes before neat benzyl bromide (84 mL, 0.7 mol) was added in one portion. An exothermic reaction was observed. After stirred overnight at room temperature, the entire mixture was dumped into an ice-water mixture (1000 mL). The crude product was extracted out with ethyl acetate (2×800 mL). The combined organic layers were washed with water, dried over sodium sulfate, filtered and evaporated to offer a brown oil. This material was mixed with 4 N HCl in dioxane (350 mL) and stirred until gas evolution was observed. 500 mL of ether was added and the precipitate was collected by filtration and washed with ether and hexane. The desired product was obtained as a hydrochloride salt (164 g, 93%). $^1$H NMR (400 MHz, $CD_3OD$): δ 7.38 (m, 5H), 6.25 (m, 1H), 5.94 (m, 1H), 5.20 (s, 2H), 4.32 (br s, 1H), 3.80 (br s, 1H), 2.67 (m, 1H), 2.14 (m, 1H).

Step B:

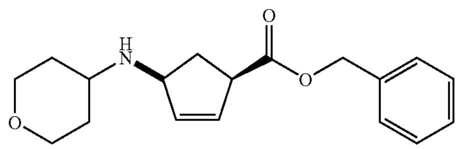

To a mixture of the amino ester HCl salt (Step A, Procedure 1-B, Intermediate 1)(38 g, 150 mmol), tetrahydro-4-H-pyran-4-one (15 g, 150 mmol), DIEA (20.6 g, 160 mmol) and 4 Å powdered molecular sieves (~20 g) in 200 mL of dichloromethane was added sodium triacetoxyborohydride (42.4 g, 200 mmol) in multiple portions. After complete addition, the mixture was stirred at room temperature overnight, quenched with saturated aqueous sodium carbonate, and filtered through celite. The crude product was extracted into dichloromethane (3×), dried over sodium sulfate and evaporated. The residue was purified by flash chromatography (silica gel, 10%[aq. NH4OH/MeOH 1/9]/DCM). The desired fractions were combined and evaporated. The resulting residue was mixed with THF and evaporated, redissolved in toluene and evaporated, and dried under vacuum to yield a light brown oil (38 g, 84%). $^1$H NMR (400 MHz, $CDCl_3$): δ 7.38 (m, 5H), 5.98 (m, 1H), 5.85 (m, 1H), 3.98 (m, 3H), 3.54 (m, 1H), 3.40 (m, 2H), 2.82 (m, 1H), 2.44 (m, 1H), 1.90 (m, 1H), 1.79 (m, 2H), 1.70 (m, 1H), 1.44 (m, 2H).

Step C:

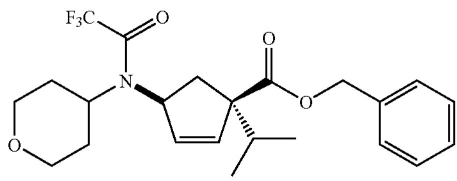

To a round bottom flask containing solid potassium bis-trimethylsilyl amide (30 g, 150 mmol) under nitrogen was added 500 mL of anhydrous THF, and the resulting solution was cooled to −78° C. A solution of the amino ester (Step B, Procedure B, Intermediate 1)(38 g, 130 mmol) in 100 mL of THF was added over 20 minutes. The dry ice-acetone bath was changed into a dry ice-water bath (~−15° C.). The mixture was stirred at −15° C. for 1 h and recooled to −78° C. A neat solution of isopropyl iodide (65 mL, 380 mmol) was added. The flask was placed into a −15° C. bath again. After a few minutes, a large amount of white precipitate was formed. The reaction mixture was stirred for additional 1 h, poured into a mixture of ice and water, and extracted with ethyl ether (3×). The ether layers were washed with water and brine, dried over sodium sulfate and evaporated. The resulting residue was dissolved in dichloromethane, dried over sodium sulfate again and evaporated. The residue was dried under vacuum, mixed with dichloromethane (200 mL) and cooled to 0° C. under nitrogen. To the solution was added pyridine (33 mL, 400 mmol) and trifluoroacetic anhydride (27 mL, 190 mmol) dropwise. After 1 h, the reaction was quenched with water. The organic phase was separated and washed with 2 N aqueous HCl, water and then brine. After being dried over sodium sulfate and evaporated, the residue was purified by flash chromatography (silica gel, 20% EtOAc/hexane) to yield an light brown oil (41 g, 74%). $^1$H-NMR showed a 5:1 mixture of cis/trans isomers. %). $^1$H NMR (400 MHz, $CDCl_3$): δ CH═CH: Cis: 6.06 (m, 1H), 5.68 (m, 1H). Trans: 5.92 (m, 0.2H), 5.79 (m, 0.2H). LC-MS for C23H28F3NO4 $[M^+H^+]$ calculated 440, found 440.

Step D:

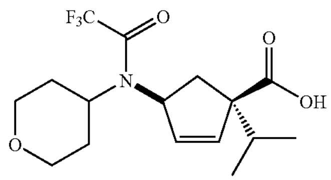

The unsaturated benzyl ester (Step C, Procedure 1-B, Intermediate 1)(41 g) and 10% Pd/C (2.0 g) in ethyl acetate (100 mL) was hydrogenated on a Parr shaker under 50 psi of hydrogen overnight. The catalyst was removed by filtration through a pad of celite. The filtrate was evaporated and dissolved in dichloromethane, evaporated and dried under vacuum overnight. The desired acid was obtained as a gummy white solid (32.5 g, 100%). LC-MS for C16H24F3NO4 $[M^+H^+]$ calculated 352, found 352.

INTERMEDIATE 2

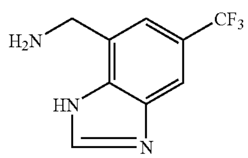

Step A:

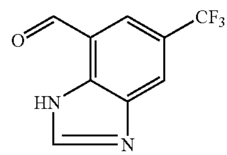

4-Bromo-6-trifluoromethyl benzimidazole (7.3 g, 28 mmol) was dissolved in THF (100 mL) and treated with sodium hydride (60% w/w in mineral oil, 1.2 g, 30 mmol) portionwise at room temperature. After 1 h the reaction was cooled to −78° C. and treated with tert-butyllithium (34 mL of 1.7 M solution in THF, 58 mmol). After 30 min at −78° C. the reaction was quenched with DMF (7.0 mL, 96 mmol) and allowed to warm to room temperature. After 12 h at room temperature the reaction was partitioned between ethyl acetate and saturated aqueous sodium bicarbonate. The organic layer was washed with brine, dried over $MgSO_4$, filtered and concentrated under reduced pressure to give 6.10 g of a crude oil.

Step B:

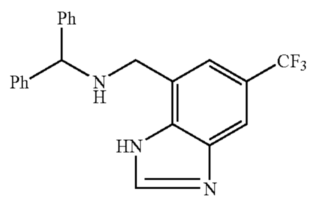

The crude oil from Step A was added to a solution of aminodiphenylmethane (4.9 mL, 28 mmol) in DCM (200 mL) and acetonitrile (40 mL). After 10 min at room temperature this reaction was treated with 4 Å molecular sieves (~2 g) and sodium triacetoxyborohydride (24 g, 110 mmol). After 72 h at room temperature the reaction was filtered through celite and washed with saturated aqueous sodium bicarbonate and brine. The aqueous layer was dried over $MgSO_4$, filtered and concentrated under reduced pressure. The crude material was purified by flash chromatography (silica gel, 2.7% MeOH/0.3% $NH_4Cl$/97% DCM) to give 4.0 g of a white solid (38% over 2 steps). ESI-MS calc. for C22H18F3N3: 381; Found 382 (M+H).

Step C:

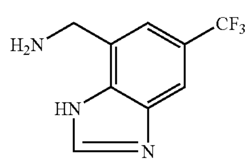

The product from Step B (2.3 g, 6.0 mmol) was dissolved in a solution of methanol (50 mL) and hydrochloric acid (concentrated aqueous solution, 0.5 mL, 6 mmol) and treated with palladium hydroxide on activated carbon (20%, 230 mg). The reaction was stirred under a hydrogen atmosphere (1 atm) for 4 h at room temperature after which time it was filtered through celite and concentrated under reduced pressure to give 2.8 g of crude product. 500 mg of this crude product was purified by reverse phase HPLC (C18, 20 to 100% MeCN/$H_2O$) and converted to its hydrochloride salt by addition of hydrogen chloride (2 N solution in ethyl ether) followed by concentration under reduced pressure to give 250 mg of a white solid (80%). ESI-MS calc. for C9H8F3N3: 215; Found 216 (M+H).

INTERMEDIATE 3

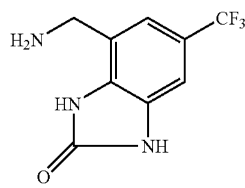

Step A:

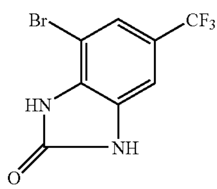

To a 0° C. solution of 3-Bromo-4,5-diaminobenzotrifluoride (4.0 g, 16 mmol) in THF (15 mL) was added carbonyl diimidazole (2.6 g, 16 mmol) in THF (20 mL) dropwise. The resultant solution was allowed to warm to room temperature. After 15 h at room temperature the reaction was treated with another portion of carbonyl diimidazole (2.6 g, 16 mmol) and allowed to stir at room temperature. When the reaction was complete by TLC (~72 h), the solution was concentrated under reduced pressure and purified by flash chromatography (silica gel, 50% EA/hexanes) to give 3.5 g of product.

ESI-MS calc. for C8H4BrF3N2: 280/282; Found 281/283 (M+H).

Step B:

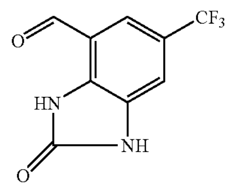

To a suspension of sodium hydride (60% w/w in mineral oil, 600 mg, 14.9 mmol) in THF (50 mL) was added the product from Step A (2.0 g, 7.1 mmol). After the cessation of hydrogen evolution, the reaction was cooled to −78° C. and tert-butyllithium (1.7 M solution in THF, 8.8 mL, 15 mmol) was added dropwise. After 30 min at −78° C. the reaction was quenched with DMF (1.8 mL, 25 mmol) and allowed to warm to room temperature. After 18 h at room temperature the reaction was concentrated to remove the THF and the crude material was partitioned between EA and saturated aqueous sodium bicarbonate. The organic layer was washed with brine and dried over $MgSO_4$, filtered and concentrated to give 1.9 g of a crude oil.

Step C:

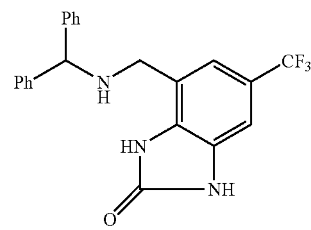

The crude oil from Step B was added to a solution of aminodiphenylmethane (1.7 mL, 9.9 mmol) in DCM (100 mL). After 10 min at room temperature this reaction was treated with 4 Å powdered molecular sieves (~1 g) and sodium triacetoxyborohydride (7.0 g, 40 mmol). After 72 h at room temperature the reaction was filtered through celite and washed with saturated aqueous sodium bicarbonate and brine. The aqueous layer was dried over $MgSO_4$, filtered and concentrated under reduced pressure. The crude material was purified by MPLC (silica gel, 1 to 10% (10% $NH_4OH$/MeOH)/DCM) to give 700 mg of a white solid (25% over 2 steps). ESI-MS calc. for C22H18F3N3O: 397; Found 398.

Step D:

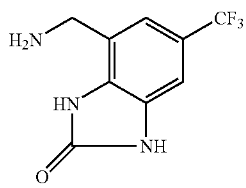

The product from Step C (700 mg, 1.7 mmol) was dissolved in a solution of methanol (20 mL) and hydrochloric acid (concentrated aqueous solution, 0.1 mL, 2 mmol) and treated with palladium hydroxide on activated carbon (20%, 150 mg). The reaction was stirred under a hydrogen atmosphere (1 atm) for 4 h at room temperature after which time it was filtered through celite and concentrated under reduced pressure to give 700 mg of crude product (58% product). ESI-MS calc. for C9H8F3N3O: 231; Found 232 (M+H).

INTERMEDIATE 4

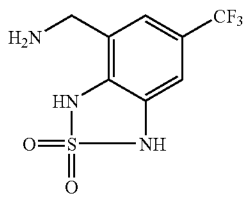

Step A:

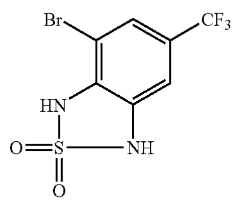

To a solution of 3-Bromo-4,5-diaminobenzotrifluoride (2.0 g, 7.8 mmol) in diglyme (30 mL) was added sulfamide (750 mg, 7.8 mmol). The resultant solution was heated to reflux for 3 h before being allowed to cool to room temperature. After 15 h at room temperature the reaction was concentrated to dryness and partitioned between EA and aqueous 2 N hydrochloric acid. The organic layer was washed with 2 N HCl twice and with a saturated solution of aqueous sodium bicarbonate followed by brine. The organic layer was dried over $MgSO_4$, filtered and concentrated under reduced pressure. The product was purified by MPLC (silica gel, 1-5% (10% MeOH NHOH)/DCM) to give 1.8 g of a solid (73%). ESI-MS calc. for C7H4BrF3N2O2S: 315/317; Found 316/318 (M+H).

Step B:

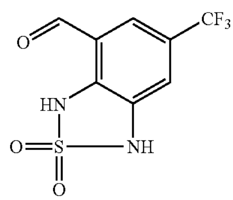

To a suspension of sodium hydride (60% w/w in mineral oil, 2670 mg, 6.6 mmol) in THF (50 mL) was added the product from Step A (1.0 g, 3.1 mmol). After the cessation of hydrogen evolution, the reaction was cooled to −78° C. and tert-butyllithium (1.7 M solution in THF, 3.9 mL, 6.6 mmol) was added dropwise. After 30 min at −78° C. the reaction was quenched with DMF (800 μL, 11 mmol) and allowed to warm to room temperature. After 3 h at room temperature the reaction was concentrated to remove the THF and the crude material was partitioned between EA and saturated aqueous sodium bicarbonate, at which point the desired product precipitated out and was filtered off to give 480 mg of a white solid (60%)

Step C:

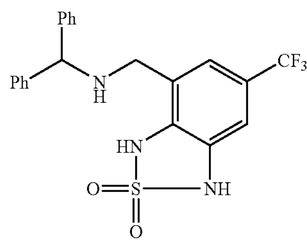

The product from Step B was added to a solution of aminodiphenylmethane (370 μL, 2.1 mmol) in methyl alcohol (100 mL). The solution was made mildly acidic with the addition of glacial acetic acid (to around pH of 4 when pH paper was saturated with $H_2O$). Sodium cyanoborohydride was added, and the resultant solution was stirred for 72 h at room temperature before being concentrated to remove the solvent. The crude product was partitioned between DCM and a saturated solution of aqueous sodium bicarbonate. The aqueous layer was washed with brine and dried over $Na_2SO_4$, filtered and concentrated under reduced pressure. The crude product was purified by reverse phase HPLC (C18, 20-100% $MeCN/H_2O$) to give 380 mg of product (49%). ESI-MS calc. for C21H18F3N3O2S: 433; Found 434.

Step D:

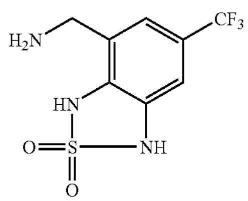

The product from Step C (380 mg, 0.9 mmol) was dissolved in a solution of methanol (10 mL) and hydrochloric acid (concentrated aqueous solution, 70 μL, 1 mmol) and treated with palladium hydroxide on activated carbon (20%, 38 mg). The reaction was stirred under a hydrogen atmosphere (1 atm) for 4 h at room temperature after which time it was filtered through celite and concentrated under reduced pressure. The crude product was purified by reverse phase HPLC (C18, 20-100% $MeCN/H_2O$) to give 200 mg of a white solid (85%), after being converted to its HCl salt by treatment with hydrogen chloride (2 N solution in ethyl ether). ESI-MS calc. for C8H8F3N3O2S: 267; Found 268 (M+H).

INTERMEDIATE 5

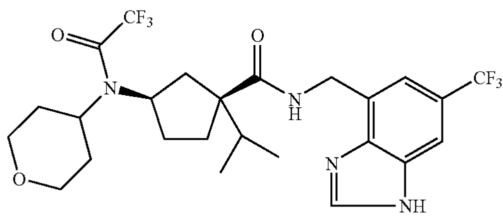

Intermediate 1 (200 mg, 0.56 mmol) was dissolved in DCM (25 mL) and cooled to 0° C. before being treated with oxalyl chloride (130 μL, 1.5 mmol) and DMF (1 drop). This solution was stirred at room temperature for 2 h and concentrated under reduced pressure. The resulting acid chloride was re-dissolved in DCM (20 mL) and added dropwise to a cooled (0° C.) solution of Intermediate 2 (215 mg, 0.86 mmol) dissolved in triethylamine (10 mL). This solution was stirred at room temperature over night before being concentrated under reduced pressure and purified by MPLC (silica gel, 1-10% (10% $NH_4OH$/MeOH)/DCM) to give 170 mg of a white solid (55%). ESI-MS calc. for C25H30F6N4O3: 548; found 549 (M+H).

INTERMEDIATE 6

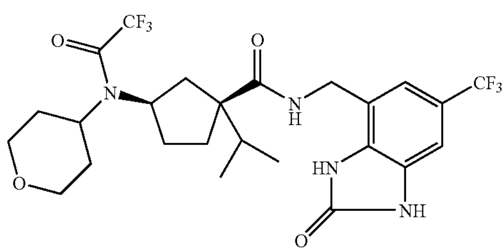

Intermediate 1 (206 mg, 0.587 mmol) was dissolved in DCM (25 mL) and cooled to 0° C. before being treated with oxalyl chloride (152 μL, 1.73 mmol) and DMF (1 drop). This solution was stirred at room temperature for 2 h and concentrated under reduced pressure. The resulting acid chloride was re-dissolved in DCM (20 mL) and added dropwise to a cooled (0° C.) solution of Intermediate 3 (270 mg, 1.00 mmol) dissolved in triethylamine (10 mL). This solution was stirred at room temperature over night before being diluted with DCM, washed with saturated aqueous sodium bicarbonate, and brine. The organic layer was dried over $Na_2SO_4$, filtered, and concentrated under reduced pressure to give 315 mg of product (95%). ESI-MS calc. for C25H30F6N4O4: 564; found 565 (M+H).

INTERMEDIATE 7

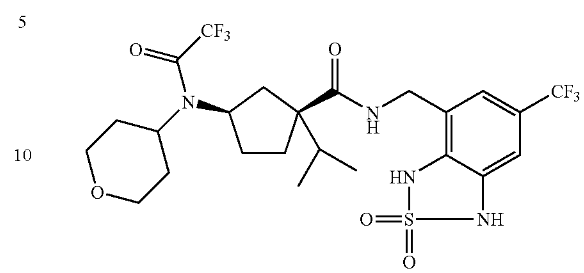

Intermediate 1 (60 mg, 0.17 mmol) was dissolved in DCM (10 mL) and cooled to 0° C. before being treated with oxalyl chloride (50 μL, 0.55 mmol) and DMF (1 drop). This solution was stirred at room temperature for 1 h and concentrated under reduced pressure. The resulting acid chloride was re-dissolved in DCM (5 mL) and added dropwise to a cooled (0° C.) solution of Intermediate 4 (73 mg, 0.27 mmol) dissolved in triethylamine (10 mL). This solution was stirred at room temperature over night before being concentrated under reduced pressure and the product purified by reverse phase HPLC (C18, 20-100% MeCN/$H_2O$) to give 45 mg of product (44%). ESI-MS calc. for C24H30F6N4O5S: 600; found 601 (M+H).

INTERMEDIATE 8

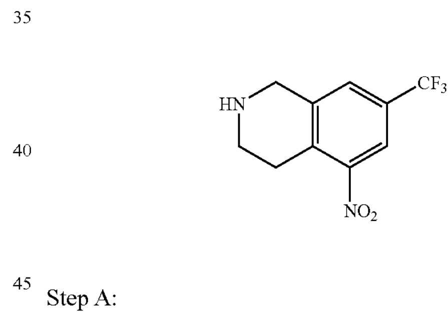

Step A:

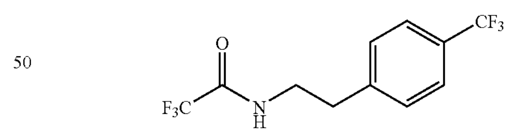

A solution of 4-trifluoromethylphenylacetonitrile (10 g, 49 mmol) in a mixture of ethanol (100 ml) and ammonium hydroxide (20 ml of a 29.3% aqueous solution) was hydrogenated over Raney nickel (~1 g) for 16 h. The catalyst was removed by filtration through celite and the filtrate was evaporated to dryness. The neat residue was added in a dropwise manner to trifluoroacetic anhydride (25 mL, 180 mmol) and cooled at 0° C. The resulting was mixture stirred at 0° C. for 30 minutes. The reaction mixture was poured onto ice (250 ml) and the resulting mixture was stirred for 30 minutes after which time the precipitate was removed by filtration and air dried to give the product as a white solid (13.4 g, 90%);

Step B:

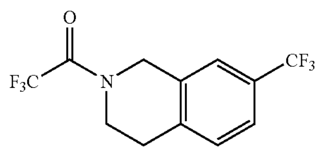

To a mixture of the product from step A (13 g, 44 mmol) and paraformaldehyde (2 g, 50 mmol) was added in one portion a mixture of concentrated sulfuric acid (90 ml) and glacial acetic acid (60 ml) and the resulting mixture was stirred at room temperature for 16-h. The reaction mixture was poured onto a mixture of ice and water (1 litre) and extracted with ethyl acetate (3×150 mL); the combined ethyl acetate layers were washed with water (3×500 mL), saturated $NaHCO_3$ (200 ml), and saturated NaCl (100 mL), dried over $MgSO_4$, filtered and evaporated in vacuo. The residue was purified by column chromatography on silica gel eluting with 10% Et2O in Hexanes to give the desired product (8.29 g, 60%).

Step C:

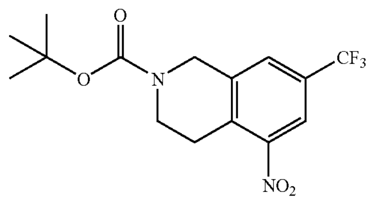

To a flask containing the product from Step B (10.0 g, 50 mmol) was added 30 mL of 70% nitric acid. The mixture was cooled at 0° C., and 30 mL of concentrated sulfuric acid was added over 30 min. The resulting solution was stirred at room temperature overnight before being poured into an ice-water mixture and made alkaline to pH>10 with solid $LiOH.H_2O$ at 0° C. Under vigorous stirring, a solution of di-tert-butyl dicarbonate (21.8 g, 100 mmol) in 500 mL of DCM was added. The mixture was stirred for 30 min, the organic layer was separated and the aqueous layer was extracted with DCM (2×200 mL). The combined extracts were washed with water (500 mL), dried over $Na_2SO_4$, and evaporated. The crude product was purified by flash chromatography (silica gel, 20% EtOAc/hexane) to give 17.0 g of a white solid. $^1$H NMR (400 MHz, $CDCl_3$) δ 8.05 (s, 1H), 7.62 (s, 1H), 4.72 (s, 2H), 3.67 (t, J=6.0 Hz, 2H), 3.13 (t, J=6.0 Hz, 2H), 1.49 (s, 9H).

Step D:

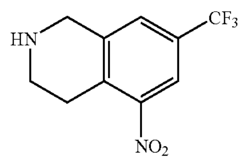

The product from Step C (17.0 g) was dissolved in 100 mL of 4 N HCl in dioxane and stirred for 1 h, evaporated and dried under vacuum. Intermediate 8 was obtained as white solid in quantitative yield. $^1$H NMR (400 MHz, $CD_3OD$) δ 8.75 (s, 1H), 8.00(s, 1H), 2.58 (s, 2H), 3.57 (t, J=6.0 Hz, 2H), 3.42 (t, J=6.0 Hz, 2H).

INTERMEDIATE 9

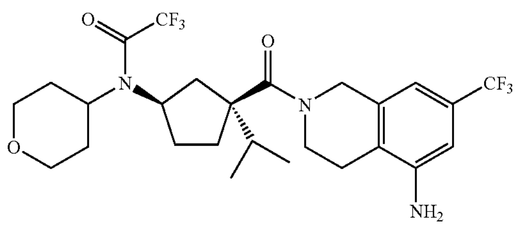

Step A:

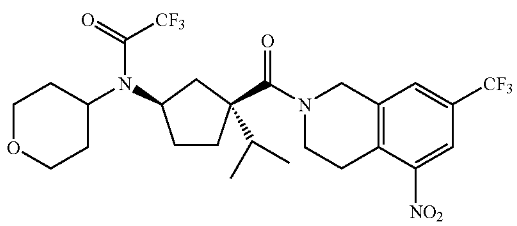

To a solution of Intermediate 1 (1.37 g, 3.89 mmol) in DCM (3 mL), was added 2.0 M oxalyl chloride in DCM (2.3 mL, 4.6 mmol) and DMF (~100 mL). The reaction mixture was stirred for 16 h, and concentrated. The residue was put under high vacuum for 2 h and dissolved in DCM (10 mL). The formed acid chloride was added into a solution of Intermediate 8 (HCl salt, 1.0 g, 3.5 mmol) and DIEA (1.54 mL, 8.84 mmol) in DCM at 0° C. The reaction mixture was stirred at room temperature for 16 h and concentrated. The residue was purified by flash column chromatography (silica gel, 30% EtOAc/hexane) to yield 1.65 g of the desired product (81%). $^1$H-NMR (500 MHz, $CDCl_3$) δ 8.16 (m, 1H), 7.64-7.71 (m, 1H), 4.80-5.20 (m, 2H), 3.84-4.20 (m, 6H), 3.56-3.73 (m, 2H), 3.45 (m, 2H), 3.18-3.36 (m, 4H), 2.71 (m, 2H), 2.40 (m, 1H), 2.00-2.14 (m, 2H), 1.86-1.97 (m, 4H), 1.52-1.72 (m, 6H), 0.86-1.04 (m, 8H). ESI-MS calc. for C26H31F6N3O5: 579.22; Found: 580 (M+H).

Step B:

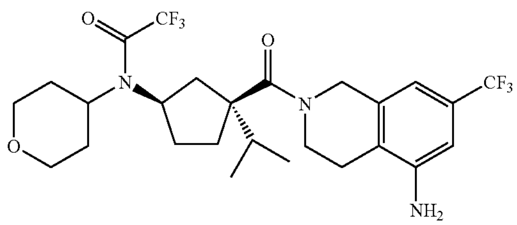

To a solution of the product prepared in Step A (1.61 g, 2.78 mmol) in ethanol (110 mL), was added 10% Pd/C (280 mg). The reaction mixture was placed in a Parr-shaker and shaken under 50 psi of H2 for 2 h. The solution was filtered through celite and concentrated under vacuum to yield Intermediate 9 (1.58 g, 100%). ESI-MS calc. for C26H33F6N3O3: 549.24; Found: 550 (M+H).

EXAMPLE 1

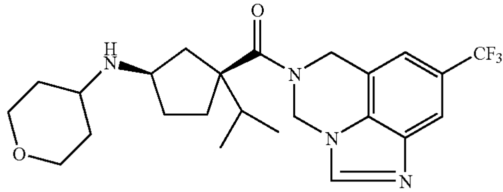

Step A:

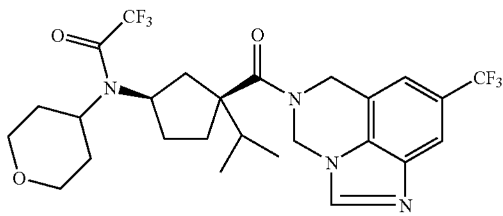

Intermediate 5 (120 mg, 0.22 mg) was added to a heterogeneous mixture of paraformaldehyde (500 mg) and p-toluene sulfonic acid (2 mg, 0.01 mmol) in toluene (10 mL) and heated to reflux in the presence of a dean-stark trap. After 18 h at reflux, the reaction was concentrated to dryness under reduced pressure. The crude product was purified by preparatory thin layer chromatography (silica gel, 1000 μm, 4.5% methyl alcohol, 0.5% $NH_4OH$, 95% DCM) to give 11 mg of the desired product (middle spot) and 90 mg of recovered starting material (Step A product, bottom spot). Middle spot: ESI-MS calc. for C26H30F6N4O3: 560; found 561 (M+H). Bottom spot: ESI-MS calc. for C25H30F6N4O3: 548; found 549 (M+H).

Step B:

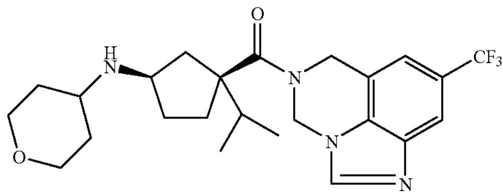

The desired product (middle spot) from Step A (11 mg, 0.020 mmol), was dissolved in ethanol (5 mL), treated with sodium borohydride (20 mg, 0.5 mmol). After 18 h at room temperature the reaction was concentrated to dryness and the resultant crude product was purified by reverse phase HPLC (C18, 20-100% $MeCN/H_2O$) to give 8 mg of a white solid, after being converted to its HCl salt by treatment with hydrogen chloride (2 N solution in ethyl ether)(85%). ESI-MS calc. for C24H31F3N4O2: 464; found 465 (M+H).

EXAMPLE 2

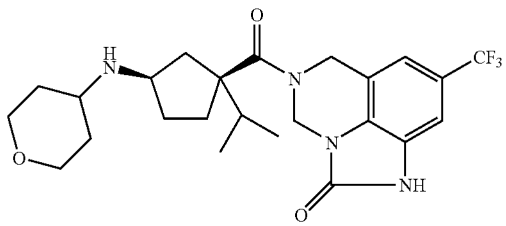

Step A:

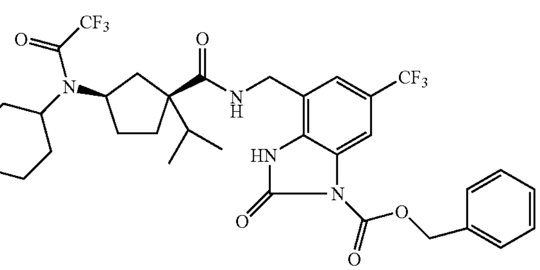

Intermediate 6 (320 mg, 0.55 mmol) was combined with benzylsuccinimidyl carbonate (190 mg, 0.76 mmol) and $K_2CO_3$-1.5$H_2O$ (110 mg, 0.55 mmol) in acetonitrile (50 mL) and heated to reflux. After 2 h the reaction was cooled to room temperature and concentrated under reduced pressure. The product was purified by medium pressure liquid chromatography (silica gel, 20-100% EA/hexanes) to give 130 mg of a colorless oil (34%) as a mixture of regio-isomers. ESI-MS calc. for C33H36F6N4O6: 698; found 699 (M+H).

Step B:

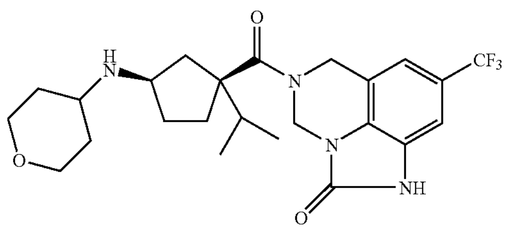

The product from Step A (130 mg, 0.19 mmol) was added to a heterogeneous mixture of paraformaldehyde (500 mg) and p-toluene sulfonic acid (2 mg, 0.01 mmol) in toluene (50 mL) and heated to reflux in the presence of a dean-stark trap. After 18 h at reflux, the reaction was concentrated under reduced pressure, diluted with DCM and washed with aqueous saturated sodium bicarbonate and brine. The aqueous layer was dried over $MgSO_4$, filtered, and concentrated under reduced pressure. The resulting residue was dissolved in ethanol (10 mL), treated with sodium borohydride (100 mg) and stirred at room temperature. After 18 h the reaction was concentrated under reduced pressure and the product was purified by reverse phase HPLC (C18, 20-100% $MeCN/H_2O$) and converted to its HCl salt by addition of hydrogen chloride (2 N in ethyl ether) to give 15 mg of a white solid (17%). ESI-MS calc. for C24H31F3N4O3: 480; found 481 (M+H).

EXAMPLE 3

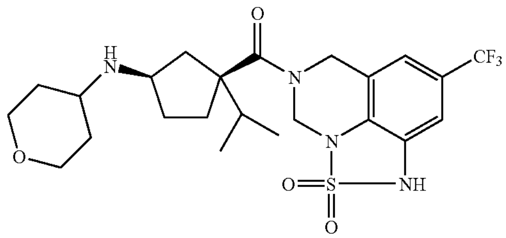

Step A:

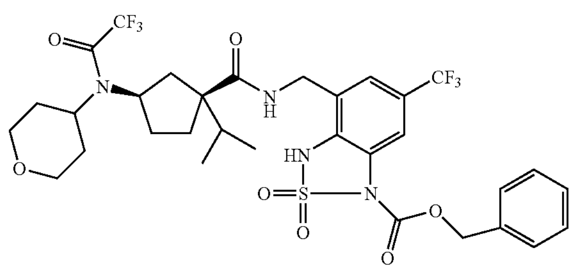

Intermediate 7 (45 mg, 0.075 mmol) was combined with benzylsuccinimidyl carbonate (22 mg, 0.090 mmol) and $K_2CO_3$-1.5$H_2O$ (13 mg, 0.094 mmol) in acetonitrile (10 mL) and heated to reflux. After 1 h the reaction was cooled to room temperature, diluted with DCM and washed with saturated aqueous sodium bicarbonate and brine. The organic layer was dried over $MgSO_4$, filtered, and concentrated under reduced pressure to give 40 mg of product as a mixture of regio-isomers (73%). ESI-MS calc. for C32H36F6N4O7S: 734; found 735 (M+H).

Step B:

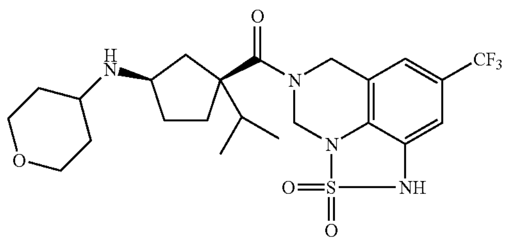

The product from Step A (40 mg, 0.054 mmol) was added to a heterogeneous mixture of paraformaldehyde (100 mg) and p-toluene sulfonic acid (1 mg) in toluene (10 mL) and heated to reflux in the presence of a dean-stark trap. After 2 h at reflux, the reaction was concentrated under reduced pressure and the resulting residue was dissolved in ethanol (10 mL), treated with sodium borohydride (40 mg) and stirred at room temperature. After 18 h the reaction was concentrated under reduced pressure and the product purified by reverse phase HPLC (C18, 20-100% MeCN/$H_2O$) and converted to its HCl salt by the addition of hydrogen chloride (2 N in ethyl ether) to give 6 mg of the desired product as a white solid (22%). ESI-MS calc. for C23H31F3N4O4S: 516.20; found 517 (M+H).

EXAMPLE 4

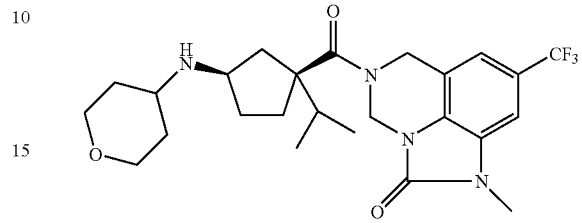

Step A:

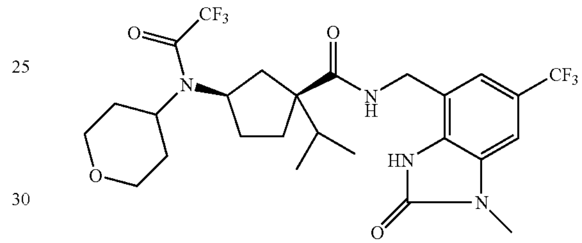

Intermediate 6 (76 mg, 0.13 mmol) was combined with methyl iodide (10 μL, 0.16 mmol) and potassium carbonate (22 mg, 0.16 mmol) in acetonitrile (5 mL) and heated to reflux. After 5 h the reaction was cooled to room temperature, concentrated under reduced pressure, and the resulting residue was partitioned between brine and DCM. The organic layer was dried over $MgSO_4$, filtered and concentrated to give 80 mg of a colorless oil as a mixture of mono-alkylation regio-isomers and some di-alkylation product which was used directly in the next step. ESI-MS calc. for C33H36F6N4O6: 698; found 699 (M+H).

Step B:

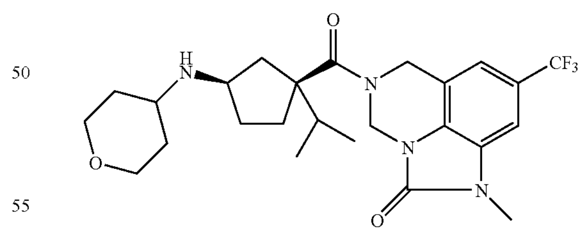

The product from Step A (80 mg, ~0.13 mmol) was added to a heterogeneous mixture of paraformaldehyde (100 mg) and p-toluene sulfonic acid (2 mg, 0.01 mmol) in toluene (25 mL) and heated to reflux in the presence of a dean-stark trap. After 2.5 h at reflux, the reaction was cooled to room temperature and concentrated under reduced pressure. The resulting residue was dissolved in ethanol (10 mL), treated with sodium borohydride (100 mg) and stirred at room temperature. After 36 h the reaction was concentrated under reduced pressure and the product was purified by reverse phase HPLC (C18, 20-100% $MeCN/H_2O$) and converted to its HCl salt by the addition of hydrogen chloride (2 N in ethyl ether) to give 1.0 mg of the desired product as white solid (2%). ESI-MS calc. for C25H33F3N4O3: 494; found 495 (M+H).

EXAMPLE 5

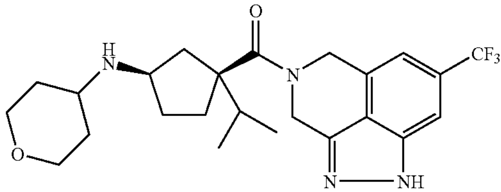

Step A:

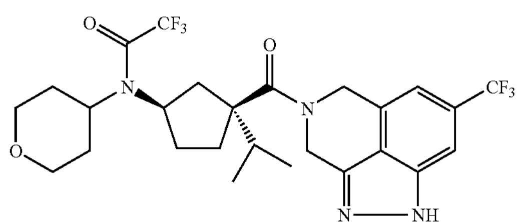

To a cooled (0° C.) solution of the Intermediate 9 (100 mg, 0.182 mmol) in acetic acid (1.5 mL) and water (5 drops) was added sodium nitrite (18.8 mg, 0.272 mmol). The reaction mixture was stirred for 0.5 h and then slowly added into a 20% sodium acetate solution at 0° C. The mixture was stirred for 0.5 h at 0° C., stirred for 1 h at room temperature and then extracted with EtOAc (twice). The combined organic layers were washed with water and brine, dried over $Na_2SO_4$, filtered and concentrated. The residue was purified by preparative TLC (silica gel, 1000 micron)(developed by 8% [aqueous $NH_4OH$/MeOH 1/9]/DCM) to yield the Intermediate 84.2 mg of the desired product (82.5%). LC-MS calc. for C26H30F6N4O3: 560.22; Found: 561 (M+H).

Step B:

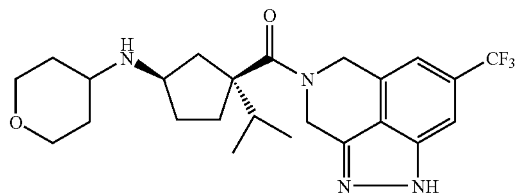

The trifluoroacetate protecting group was removed from the product of the previous step according to the procedure described in Example 1. ESI-MS calc. for C24H31F3N4O2: 464.24; Found: 465 (M+H).

What is claimed is:

1. A compound of the formula II

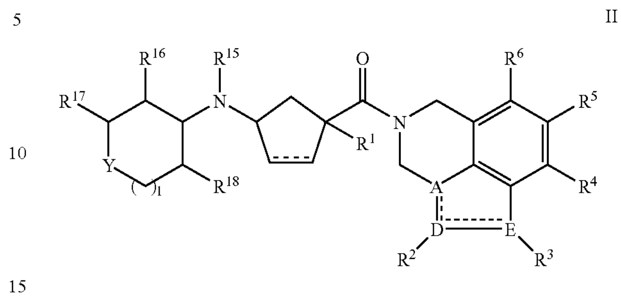

wherein:

A is selected from the group consisting of C and N;

D is independently selected from the group consisting of C, N, O, —SO— and —$SO_2$—, E is N;

Y is selected from the group consisting of —$CH_2$— and —O—;

$R^1$ is selected from the group consisting of:
- (a) $C_{1-6}$alkyl,
- (b) $C_{1-6}$alkyl substituted with hydroxy, and
- (c) $C_{1-6}$alkyl substituted with 1-6 fluoro;

if D is C, $R^2$ is selected from the group consisting of:
- (a) hydrogen,
- (b) $C_{1-3}$alkyl, optionally substituted with 1-3 fluoro,
- (c) —O—$C_{1-3}$alkyl, optionally substituted with 1-3 fluoro,
- (d) hydroxy,
- (e) chloro,
- (f) fluoro,
- (g) bromo,
- (h) phenyl, and
- (i) =O;

if D is N, $R^2$ is selected from the group consisting of:
- (a) hydrogen,
- (b) $C_{1-3}$alkyl, optionally substituted with 1-3 fluoro,
- (c) —O—$C_{1-3}$alkyl, optionally substituted with 1-3 fluoro,
- (d) phenyl,
- (e) O, and
- (f) nothing;

if D is O, SO, or $SO_2$, $R^2$ is nothing;

$R^3$ is selected from the group consisting of:
- (a) hydrogen,
- (b) $C_{1-3}$alkyl, optionally substituted with 1-3 fluoro,
- (c) —O—$C_{1-3}$alkyl, optionally substituted with 1-3 fluoro,
- (d) phenyl,
- (e) O, and
- (f) nothing;

if E is O, SO, or $SO^2$, $R^3$ is nothing;

$R^4$ is hydrogen;

$R^5$ is selected from the group consisting of:
- (a) $C_{1-6}$alkyl substituted with 1-6 fluoro,
- (b) —O—$C_{1-6}$alkyl substituted with 1-6 fluoro,
- (c) chloro,
- (d) bromo, and
- (e) phenyl;

$R^6$ is hydrogen;

$R^{15}$ is selected from the group consisting of hydrogen and methyl;

$R^{16}$ is selected from the group consisting of:
(a) hydrogen,
(b) $C_{1-3}$alkyl, which is unsubstituted or substituted with 1-6 fluoro,
(c) —O—$C_{1-3}$alkyl,
(d) fluoro, and
(e) hydroxy;

$R^{17}$ is hydrogen;

$R^{18}$ is selected from the group consisting of:
(a) hydrogen,
(b) methyl, and
(c) methoxy; and
1 is 1;

or a pharmaceutically acceptable salt or individual diastereomer thereof.

2. The compound of claim 1 of the formula IIa:

IIa

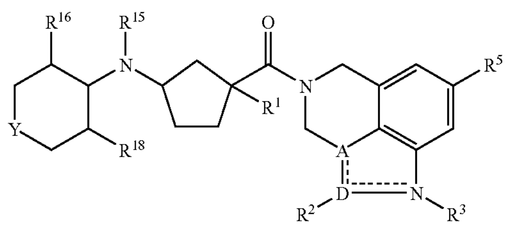

or a pharmaceutically acceptable salt or individual diastereomer thereof.

3. The compound of claim 1 of the formula IIb:

IIb

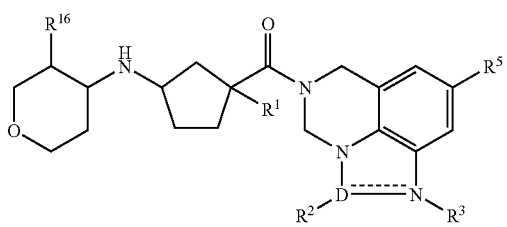

or a pharmaceutically acceptable salt or individual diastereomer thereof.

4. A compound selected from

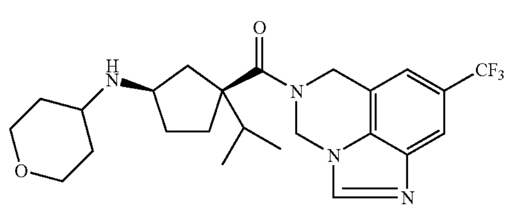

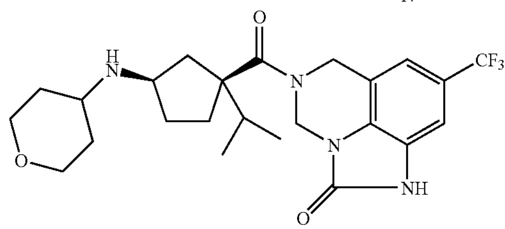

-continued

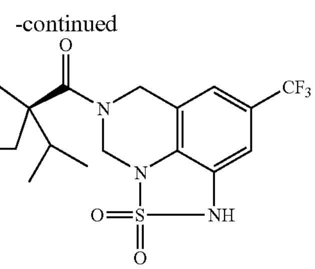

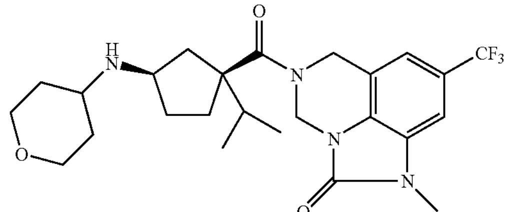

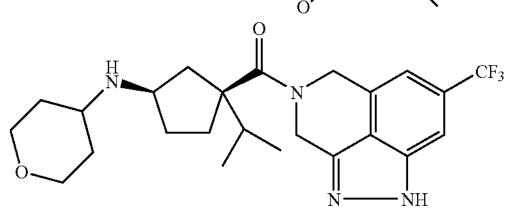

or a pharmaceutically acceptable salt or individual diastereomer thereof.

5. A pharmaceutical composition which comprises an inert carrier and a compound of claim 1.

6. The compound of claim 1, wherein A is N.

7. The compound of claim 1, wherein D is selected from the group consisting of C, N, and $SO_2$.

8. The compound of claim 1, wherein $R^1$ is selected from the group consisting of:
(a) —$CH(CH_3)^2$,
(b) —$CH(OH)CH_3$, and
(c) —$CH_2CF_3$.

9. The compound of claim 1, wherein when D is C, $R^2$ is hydrogen, hydroxy, or oxo.

10. The compound of claim 1, wherein when D is N, $R^2$ is hydrogen or is nothing.

11. The compound of claim 1, wherein $R^3$ is hydrogen or methyl.

12. The compound of claim 1, wherein $R^5$ is selected from the group consisting of:
(a) trifluoromethyl,
(b) trifluoromethoxy,
(c) chloro,
(d) bromo, and
(e) phenyl.

13. The compound of claim 1, wherein $R^5$ is trifluoromethyl.

14. The compound of claim 1, wherein $R^{16}$ is selected from the group consisting of:
(a) hydrogen,
(b) trifluoromethyl,
(c) methyl,
(d) methoxy,
(e) ethoxy,
(f) ethyl,
(g) fluoro, and
(h) hydroxy.

15. The compound of claim 1, wherein $R^{18}$ is hydrogen.

* * * * *